US012721761B2

(12) United States Patent
Tallman et al.

(10) Patent No.: US 12,721,761 B2
(45) Date of Patent: Sep. 1, 2026

(54) EASY CHANGE PROTECTIVE UNDERWEAR

(71) Applicant: Medline Industries, Inc., Northfield, IL (US)

(72) Inventors: Amanda Tallman, Kenosha, WI (US); William Rovero, Douglasville, GA (US); Kristy Matus, Grayslake, IL (US); Stuart Schneider, Pleasant Prairie, WI (US); Sharbel Maalouf, Pleasant Prairie, WI (US); Amanda Roszkowiak, Chicago, IL (US)

(73) Assignee: Medline Industries, LP, Northfield, IL (US)

( * ) Notice: Subject to any disclaimer, the term of this patent is extended or adjusted under 35 U.S.C. 154(b) by 0 days.

(21) Appl. No.: 16/773,775

(22) Filed: Jan. 27, 2020

(65) Prior Publication Data

US 2020/0155373 A1 May 21, 2020

Related U.S. Application Data

(63) Continuation-in-part of application No. 16/113,008, filed on Aug. 27, 2018, now Pat. No. 11,246,767.

(51) Int. Cl.
*A61F 13/496* (2006.01)
*A61F 13/15* (2006.01)
(Continued)

(52) U.S. Cl.
CPC .. *A61F 13/49061* (2013.01); *A61F 13/49007* (2013.01); *A61F 13/622* (2013.01);
(Continued)

(58) Field of Classification Search
CPC .......... A61F 13/49061; A61F 13/49007; A61F 13/622; A61F 2013/1591
See application file for complete search history.

(56) References Cited

U.S. PATENT DOCUMENTS 3,424,162 A 1/1969 Parravicini
4,122,552 A 10/1978 Tedford
(Continued)

FOREIGN PATENT DOCUMENTS

CN 202489181 U 10/2012
EP 0405575 B1 9/1993
(Continued)

OTHER PUBLICATIONS

"Sever." dictionary. cambridge.org, Cambridge Dictionary, https://dictionary.cambridge.org/dictionary/english/severing. Accessed Aug. 24, 2023.*

(Continued)

*Primary Examiner* — Michele Kidwell
(74) *Attorney, Agent, or Firm* — SandBright Intellectual Property; Robert D. Spendlove

(57) ABSTRACT

A disposable absorbent article, including cohesive material side panels is presented in a protective underwear style to the user. The user may don the article in the same manner as a brief style undergarment or may tear the side panels and don the article in the same manner as a diaper by cohesively attaching the torn side panels. Optionally, the users may don the article in the same manner as a brief or protective underwear style article, tear at least one side panel and adjust the sizing of the side panel by cohesively reattaching the torn side panel.

20 Claims, 17 Drawing Sheets

(51) Int. Cl.

| | |
|---|---|
| ***A61F 13/474*** | (2006.01) |
| ***A61F 13/49*** | (2006.01) |
| ***A61F 13/514*** | (2006.01) |
| ***A61F 13/62*** | (2006.01) |

(52) U.S. Cl.

CPC ............... *A61F 2013/15869* (2013.01); *A61F 2013/1591* (2013.01)

(56) References Cited

U.S. PATENT DOCUMENTS 4,560,381 A 12/1985 Southwell
4,615,695 A 10/1986 Cooper
4,641,381 A 2/1987 Heran et al.
4,674,135 A 6/1987 Greene
4,745,636 A 5/1988 Lunt
4,895,569 A 1/1990 Wilson et al.
4,938,753 A 7/1990 Gompel et al.
5,085,655 A 2/1992 Mann et al.
5,103,501 A 4/1992 Meisels
5,370,634 A 12/1994 Ando et al.
5,415,649 A 5/1995 Watanabe et al.
5,531,732 A 7/1996 Wood
5,683,373 A 11/1997 Darby
6,113,717 A 9/2000 Vogt et al.
6,182,290 B1 2/2001 Morris
6,240,569 B1 6/2001 Van Gompel et al.
6,247,184 B1 6/2001 Watts
6,419,667 B1 7/2002 Avalon et al.
6,478,786 B1 11/2002 Glaug et al.
6,560,786 B2 5/2003 Lipton
6,579,275 B1 6/2003 Pozniak et al.
6,579,949 B1 6/2003 Hergenrother et al.
6,682,626 B2 1/2004 Mlinar et al.
6,761,711 B1 7/2004 Fletcher et al.
6,849,067 B2 2/2005 Fletcher et al.
6,976,978 B2 12/2005 Ruman et al.
6,994,761 B2 2/2006 Klemp et al.
7,150,730 B2 12/2006 Hasler et al.
7,150,731 B2 12/2006 Cazzato et al.
7,175,584 B2 2/2007 Maxton et al.
7,318,820 B2 1/2008 Lavon et al.
7,344,524 B2 3/2008 Cazzato et al.
7,377,914 B2 5/2008 Lavon
7,618,404 B2 11/2009 Lavon et al.
7,737,324 B2 6/2010 Lavon et al.
8,029,488 B2 10/2011 Ashton et al.
8,043,274 B2 10/2011 Mlinar et al.
8,070,738 B2 12/2011 Ashton et al.
8,118,799 B2 2/2012 Datta et al.
8,545,474 B2 10/2013 Schilpp et al.
8,601,665 B2 12/2013 Lavon et al.
8,617,131 B2 12/2013 Kline et al.
8,632,516 B2 1/2014 Ashton et al.
8,663,415 B2 3/2014 Thorson et al.
8,684,990 B2 4/2014 Lavon et al.
8,747,379 B2 6/2014 Fletcher et al.
D768,958 S 10/2016 Dickson
D771,351 S 11/2016 Colon
D793,029 S 8/2017 Dickson
9,724,251 B2 8/2017 Lavon et al.
9,789,010 B2 * 10/2017 Long ..................... A61F 13/496
11,246,767 B2 * 2/2022 Roszkowiak ......... A61F 13/496
2002/0099353 A1 7/2002 Olson
2002/0111596 A1 8/2002 Fletcher et al.
2002/0112276 A1 8/2002 Ruman et al.
2002/0151858 A1 * 10/2002 Karami ............. A61F 13/49019 604/389
2002/0165514 A1 11/2002 Datta et al.
2003/0066122 A1 4/2003 Niedermeyer
2003/0088223 A1 * 5/2003 Vogt .................. A61F 13/15756 604/385.01
2003/0125702 A1 7/2003 Couture-Dorschner et al.
2003/0130641 A1 * 7/2003 Richlen ................. A61F 13/496 604/386
2004/0082933 A1 * 4/2004 Karami ............... A61F 13/5644 604/393
2005/0055005 A1 3/2005 Cazzato et al.
2005/0131364 A1 6/2005 Sakaguchi et al.
2005/0192553 A1 9/2005 Hasler et al.
2005/0277905 A1 12/2005 Pedersen et al.
2006/0068168 A1 3/2006 Olson et al.
2006/0148362 A1 7/2006 Bridges
2006/0218700 A1 10/2006 Uda
2006/0247595 A1 11/2006 Kawakami
2007/0049896 A1 * 3/2007 Mills ................... A61F 13/5638 604/389
2007/0049897 A1 3/2007 Lavon et al.
2007/0066951 A1 3/2007 Lavon et al.
2007/0173780 A1 7/2007 Lavon
2007/0250032 A1 10/2007 Andrews
2008/0065042 A1 * 3/2008 Wood .................... A61F 15/001 604/392
2009/0069768 A1 3/2009 Hunt
2009/0082749 A1 3/2009 Scott et al.
2009/0131902 A1 5/2009 Giloh
2009/0204088 A1 8/2009 Stearman et al.
2009/0240226 A1 9/2009 Fields et al.
2010/0125264 A1 5/2010 Naylor
2010/0241096 A1 9/2010 Lavon et al.
2010/0324517 A1 12/2010 Lenhult et al.
2011/0071487 A1 3/2011 Sabiston, Jr.
2011/0178485 A1 7/2011 Lavon et al.
2011/0178486 A1 7/2011 Lavon et al.
2011/0178490 A1 7/2011 Lavon et al.
2011/0202030 A1 * 8/2011 Ronstrom ............. A61F 13/505 604/385.14
2012/0046634 A1 2/2012 Shields
2012/0123376 A1 5/2012 Alves
2012/0152436 A1 6/2012 Schneider
2013/0012907 A1 1/2013 Sasayama et al.
2013/0072888 A1 3/2013 Zorin
2013/0165898 A1 6/2013 Rhodes et al.
2013/0230835 A1 9/2013 Ellefson et al.
2013/0231625 A1 9/2013 Ellefson et al.
2014/0039432 A1 2/2014 Dunbar et al.
2014/0187405 A1 7/2014 Volp et al.
2014/0257231 A1 * 9/2014 Wang ................ A61F 13/49006 604/394
2015/0272788 A1 10/2015 Long et al.
2016/0100989 A1 * 4/2016 Seitz ................. A61F 13/55105 604/374
2016/0168433 A1 6/2016 Himmelberger et al.
2016/0250085 A1 9/2016 Lavon et al.
2016/0331600 A1 * 11/2016 Polidori ............ A61F 13/49061
2017/0035625 A1 2/2017 Lavon et al.
2017/0156943 A1 * 6/2017 Muthu .................... A61F 13/66
2019/0365575 A1 * 12/2019 Johnson ............ A61F 13/15747
2019/0374397 A1 * 12/2019 Tally ..................... A61F 13/493
2020/0155368 A1 * 5/2020 Zink ................. A61F 13/15593
2020/0155373 A1 5/2020 Tallman et al.

FOREIGN PATENT DOCUMENTS

EP 0705088 B1 5/1999
EP 1027874 A2 8/2000
EP 1702598 A1 9/2006
WO 2005016037 A1 2/2005
WO 2005/077313 * 8/2005 ............. A61F 13/58

OTHER PUBLICATIONS

"Tear." Merriam-Webster.com Dictionary, Merriam-Webster, https://www.merriam-webster.com/dictionary/tear. Accessed Jan. 13, 2025.*

"Break." Merriam-Webster.com Dictionary, Merriam-Webster, https://www.merriam-webster.com/dictionary/break. Accessed Jan. 13, 2025.*

International Search Report and Written Opinion of the International Searching Authority, International Patent Application No. PCT/US2019/048643, Medline Industries, Inc., Dec. 13, 2019.

* cited by examiner 710
791
700
708

710
702
791
704
706
708

710
717
791
715
721
719
704
713
706
738
711
702
700
708

710
742
715
791
719
713
711
706
740

800
826
811
802
828
808
810
818
824
822
806
814
820
812
832
830
804

800
808
826
813
802
828
810
818
824
822
806
814
820
812
832
830
804

EASY CHANGE PROTECTIVE UNDERWEAR

CROSS-REFERENCE TO RELATED APPLICATIONS

This application is a continuation-in-part of U.S. patent application Ser. No. 16/113,008 filed 27 Aug. 2018 entitled "EASY CHANGE PROTECTIVE UNDERWEAR," which is incorporated herein by reference.

FIELD OF THE INVENTION

Embodiments of the present invention relate primarily to absorbent articles such as disposable incontinence articles, namely, disposable underwear side portions capable of modification to provide a more customized fit.

BACKGROUND OF THE INVENTION

Disposable absorbent articles are well known in the prior art and have many uses. Whether intended for infants, children, adults or the elderly, disposable pads, napkins, diapers, training pants, briefs, underwear, incontinence articles, and the like are intended to absorb and retain body discharges. As used herein, "absorbent article" will refer to all these examples.

Conventional diaper style absorbent articles typically include a front waist portion and a back waist portion which are releasably connected about the hips of the wearer during use by conventional fasteners such as adhesive tape fasteners or hook and loop type fasteners, et al. For example, the conventional fasteners typically include a pair of fasteners, located on the outermost corners of the diaper in the back waist region of the diaper and complimentary fasteners located on the front waist region.

In such a configuration, the diaper is positioned between the legs of the wearer and the fasteners are releasably attached to secure the diaper around the waist of the wearer. Such conventional diapers are easy to fasten and remove from the wearer after use. However, such conventional diapers are not provided in a pre-fastened configuration and, thus, are not configured to be pulled up or down over the hips of the wearer when the fasteners are attached.

Active adults appreciate the freedom afforded to them by incontinence absorbent articles. Such disposable articles can alleviate some of the emotional and physical discomfort of incontinence by absorbing and containing biomatter. Problems arise, however, when an active adult user must take advantage of public restrooms.

Disposable absorbent articles having the look and feel of traditional undergarments as opposed to diapers with side fastening systems are desirable by active adult users because such brief style absorbent articles may be pulled up or down over the hips of a wearer in the same manner as a traditional undergarment.

Similarly, brief style undergarments typically do not have the same bulk as traditional diaper style absorbent articles. Brief style absorbent articles often are configured to closely conform to the body of the wearer and consequently have a discreet profile under a wearer's clothing, which renders the absorbent article unnoticeable to the casual observer.

Such brief style absorbent articles are typically manufactured to include a plurality of side panels to connect the front portion left and right sides with the rear portion left and right sides. Such articles are typically manufactured in a pre-joined configuration, with side seams extending either toward the wearer (on an inside surface of the assembled article) or away from the wear (on an outside surface of the assembled article). Side seams are typically welded, bonded or adhered together and are therefore not adjustable. Further, side seams may not be designed to withstand repeated pulling up and down over a wearer's buttocks and hips without resulting inside seam failure.

Regardless of whether the side seams rupture, a wearer is presented with the problem of how to doff a used absorbent article and don an unused article in a public restroom setting without lowering clothing from about the waist and removing the clothing from about the ankles and feet.

Other brief style absorbent articles may include both side seams and secondary mechanical fasteners, for example hook and loop or releasable adhesive tape fasteners. Once a side seam is ruptured, a user relies upon a secondary fastener to maintain the absorbent article around the waist. Such fasteners, however, may have a tendency to attach to undesired locations, such as a wear's skin or clothing. Further, secondary fasteners may lack sufficient peel strength. If peel forces are too low, the act of lowering an absorbent article in a brief style condition may cause the fastener connection to rupture. Further, mechanical fasteners typically do not include stretch properties. Accordingly, when utilized, the mechanical fastener may not provide the same fit and comfort as the originally sealed side seams. Further, secondary mechanical fasteners can be a skin irritant.

The use of secondary mechanical fastener also offers a manufacturing disadvantage. Not only do they increase the materials production cost of the absorbent article, high speed operations during manufacture may damage mechanical fasteners.

To doff a used brief style absorbent article in restroom settings, a user can optionally remove shoes and lower garments and pull the absorbent article down over hips and buttocks to facilitate removal. In a public restroom setting, a user's clothing and stocking or bare feet can come into contact with a restroom floor, which can be both unpleasant and unsanitary. Still further, a user must expend considerable time doffing and donning clothing.

To save time, the user can optionally tear the absorbent article side seams and remove the soiled article, but the user is now faced with the challenge of how to don a new brief style absorbent article. To facilitate donning a new brief style absorbent article a user must still doff shoes and clothing.

A further problem relates to the size of public restroom stalls. Stalls typically include barely enough room for a person to enter a stall, let alone move sufficiently in front of a toilet bowl behind a closed door to remove clothing. In some rest room spaces the mere act of squatting and bending forward to maintain balance could result in a user's head coming in contact with the stall door.

Brief style absorbent articles often include an elasticized waist opening that when elongated expands to fit over the user's buttocks and hips. Accordingly, the act of doffing and donning brief style absorbent articles requires a user to stretch open the elastic waist opening, lift their feet and legs within an awkward, confined restroom stall space—without losing balance or falling—and inserting or withdrawing feet and legs into or from not only the elasticized waist opening, but also elasticized leg openings without touching any unpleasant or unsanitary surfaces within the stall. Such gymnastics, when performed by a person with normal agility within a confined space can be awkward at best. When performed by a person with diminished agility or flexibility of movement can lead to a risk of falls or injury.

Accordingly, there is a need for a brief style absorbent article that can be donned and doffed like brief style undergarments while also having the capability of transforming into a diaper style absorbent article that can be applied or removed without removal of a user's lower clothing from about the ankles and feet. As a result, the user can determine whether the article will be applied in a brief configuration or in a diaper configuration.

It is further contemplated that in accordance with embodiments of the present invention, a brief style absorbent article is provided with side panels which may be adjusted to improve the fit or comfort about the waist area of a user.

In embodiments of the present invention, absorbent articles require fewer components and materials to manufacture, thereby reducing manufacturing time, cost and impact on the environment.

To create multiple sizes, multiple size components are required, leading to an inefficient manufacturing process. Each size requires the manufacturer to stop the machine and change out a number of the machine's sections in order to produce the next size. After changing the machine sections, other sections need to be recalibrated in order to ensure the raw material components are converted correctly. These changeovers can take anywhere between six to twelve hours depending on the machine being used by the manufacturer. This downtime reduces the amount of product the machine can produce and increases the manufacturers converting cost. Further, current adult brief machines manufactures are required to use extra steel and other materials in order to build the additional components for the additional sizes.

In accordance with embodiments disclosed herein, the machine assembling the article is set such that the side panel widths are changed from a first width to a second width in order to change over from building a first article size to a second article size. Similarly, when changing over to a third article size, the side panel widths are increased, and additionally in this embodiment, the chassis length is increased to the second chassis length as for the third article size and fourth article size. For these changes, the changeover is completed by running different programs in the machine and minimal or even zero hard tooling changeover is required. By way of example, there may be no hard tool changeovers such as the replacement of cutting dies. Instead, only vacuum plate changes may be needed for the size changes in the side panel widths and length which are relatively simple replacements. In some embodiments, the vacuum plates need not even be physically replaced, the vacuum plates are sized to accommodate all sizes of side panels and depending on the size of the side panel, and vacuum ports are enabled or disable based on the size of the side panel.

BRIEF DESCRIPTION OF THE DRAWINGS

The various aspects, features and advantages of the disclosure will become more fully apparent to those having ordinary skill in the art upon careful consideration of the following Detailed Description thereof with the accompanying drawings described below.

Figure 1:
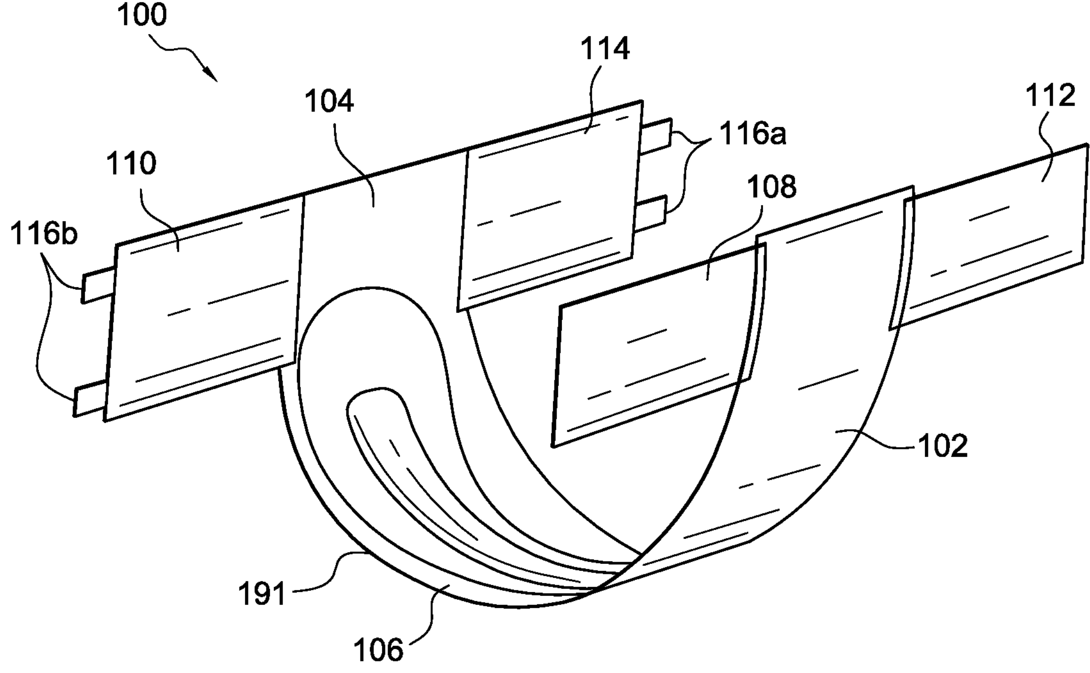
FIG. 1 is a perspective view of a diaper style absorbent article.

While embodiments of the invention are susceptible to various modifications and alternative forms, specific embodiments have been shown by way of example in the drawings and will be described in detail herein. It should be understood however, that the invention is not intended to be limited to the particular forms disclosed. Rather, the invention will cover all modifications, equivalents, and alternatives falling within the spirit and scope of the invention.

DETAILED DESCRIPTION

Embodiments of the invention are now described in detail. Referring to the drawings, like numbers indicate like parts throughout the views. As used in the description herein and throughout the claims, the following terms take the meanings explicitly associated herein, unless the context clearly indicates otherwise: the meaning of "a," "an," and "the" includes plural reference, the meaning of "in" includes "in" and "on." Relational terms such as first and second, top and bottom, left and right and the like may be used solely to distinguish one entity or action from another entity or action without necessarily requiring or implying any actual such relationship or order between such entities or actions.

As used herein, the following terms have the following meanings:

"Attach" and its derivatives refer to the joining, adhering, connecting, bonding, sewing together, or the like, of two elements. Two elements will be considered to be attached together when they are integral with one another or attached directly to one another or indirectly to one another, such as when each is directly attached to intermediate elements. "Attach" and its derivatives include permanent, releasable, or refastenable attachment. In addition, the attachment can be completed either during the manufacturing process or by the end user.

"Bond" and its derivatives refer to the joining, adhering, connecting, attaching, sewing together, or the like, of two elements. Two elements will be considered to be bonded together when they are bonded directly to one another or indirectly to one another, such as when each is directly bonded to intermediate elements. "Bond" and its derivatives include permanent, releasable, or refastenable bonding.

"Cohesive material" refers to a material which demonstrates surface interaction (in terms of connection of one surface to another) when applied to a specially selected material. Cohesive material will fasten or form a connection primarily to itself or to similarly structured materials. Generally, such materials are substantially non-tacky (such as to skin) at room temperature even under some pressure. For purposes of the present specification, the term cohesive will include materials which are sometimes referred to as "selectively adhesive" or "selective adhesive" materials. Materials which are designed to receive (i.e. allow the surface interaction) with a particular cohesive material, but which themselves will not connect with any other materials (or itself) are still considered "cohesive materials" within the meaning of this specification when they act as the target surface for a specific cohesive engaging material. Because the cohesive material will connect or fasten to selective materials and not to other materials generally, this allows for disposition of cohesive polymers onto multiple surfaces of a target material. By contrast, most mechanical fastening systems (such as hook and loop systems) require that the complimentary components be mated in only one relationship to work properly. Cohesive materials may be a bandage type cohesive material or other appropriate cohesive materials.

"Connect" and its derivatives refer to the joining, adhering, bonding, attaching, sewing together, or the like, of two elements. Two elements will be considered to be connected together when they are connected directly to one another or indirectly to one another, such as when each is directly connected to intermediate elements. "Connect" and its derivatives include permanent, releasable, or refastenable connection. In addition, the connecting can be completed either during the manufacturing process or by the end user.

"Integral" is used to refer to various portions of a single unitary element rather than separate structures bonded to or placed with or placed near one another.

"Extensible" refers to materials which elongate or increase in at least one dimension when subject to an external pulling force.

"Elastic," "elasticized" and "elasticity" mean that property of a material or composite by virtue of which it tends to recover its original size and shape after removal of a force causing a deformation.

"Elastomeric" refers to a material or composite which can be elongated by a percent of its relaxed length and which will recover, upon release of the applied force by a percent of its elongation. In certain embodiments, an elastomeric material or composite may be capable of being elongated by at least 100 percent, in further embodiments by at least 300 percent of its relaxed length. Embodiments of the elastic material or composite may recover, upon release of an applied force, at least 50 percent of its elongation.

As used herein the term "refastenable" refers to the attachment of two or more elements or portions of elements together in a manner in which they can be separated and re-attached successively without substantial degradation of fastener performance or damage to surrounding components of the article which would impair its continued use. It will be appreciated that a refastenable component need not have an infinite life span, but it is sufficient that the components attached in a refastenable manner can be separated and re-attached successively several times over the typical use life span of the article. It will also be appreciated that the aggressiveness of actual fastening or tack may be reduced significantly from fastening to refastening in absolute terms, but that such reduction is not substantial degradation of fastener performance if the resulting refastened strength is sufficient for its purpose of use in a disposable absorbent article.

"Stretchable" or "elastic" are intended to be interchangeable and refer to materials which are extensible and which also return to substantially their original dimensions when the external pulling force is removed. It will be appreciated that the terms stretchable and elastic include the term extensible as each term is used herein.

These terms may be defined with additional language elsewhere in the specification.

Absorbent articles as described herein generally include a moisture-pervious inner layer, an absorbent layer, and a liquid-impervious outer layer. Although the remainder of the description will be specifically directed to adult incontinence articles, including disposable briefs and underwear (whether intended for men or women), which may be used interchangeably herein, it is understood that the embodiments may also be implemented on other absorbent articles, whether intended for infants, children, adults or the elderly. As would be understood by one of ordinary skill in the art, such non-limiting examples include: diapers, training pants, and the like which are intended to absorb and retain body discharges.

It should be observed that the embodiments reside primarily in the combinations of assembly components and method steps for using various embodiments of the absorbent articles disclosed herein. Accordingly, the assembly components and the method steps have been represented (where appropriate) by conventional symbols in the drawings, showing only those specific details that are pertinent to understanding the embodiments of the present invention so as not to obscure the disclosure with details that will be readily apparent to those of ordinary skill in the art having the benefit of the description herein.

FIG. 1 illustrates a disposable diaper 100 configuration of an absorbent article, including a chassis 191 having a front portion 102, a rear portion 104, a crotch portion 106 extending longitudinally between the front portion 102 and the rear portion 104 wherein at least a portion of the chassis 191 is configured to absorb body discharges. Extending laterally from the front and rear portion left and right sides are side panels 108, 110, 112, 114. Complementary mechanical fastening elements 116 may be attached to one or more of the side panels 108, 110, 112, 114. In the illustrative embodiment, left side complementary fasteners **116*a* are attached to left side rear side panel 114, and right side complementary fasteners 116*b* are attached to the right side rear side panel 110**.

In use, the diaper 100 chassis 191 is inserted between the wearer's legs with the diaper rear portion 104 covering at least a portion of the wear's buttock region and the diaper front portion 102 covering at least a portion of the wearer's front pelvic region. To secure a diaper 100 around a wearer's waist and leg regions, left side front and rear side panels 112, 114 are joined. This joining may be accomplished by attachment of the left side complementary fasteners 116*a* to an outside surface of left side front side panel 112 and attachment of the right side complementary fasteners 116*b* to an outside surface of right side front side panel 108. To remove a soiled diaper 100, clothing is lowered from about the waist and gathered about the ankles, the diaper fasteners 116 are released and the diaper 100 is removed from between the wearer's legs. Optionally, the diaper fasteners 116 can be released and refastened, allowing the wearer or caregiver to inspect the diaper 100 interior and then refasten the diaper 100 if the diaper 100 remains in a use condition.

Figure 2:
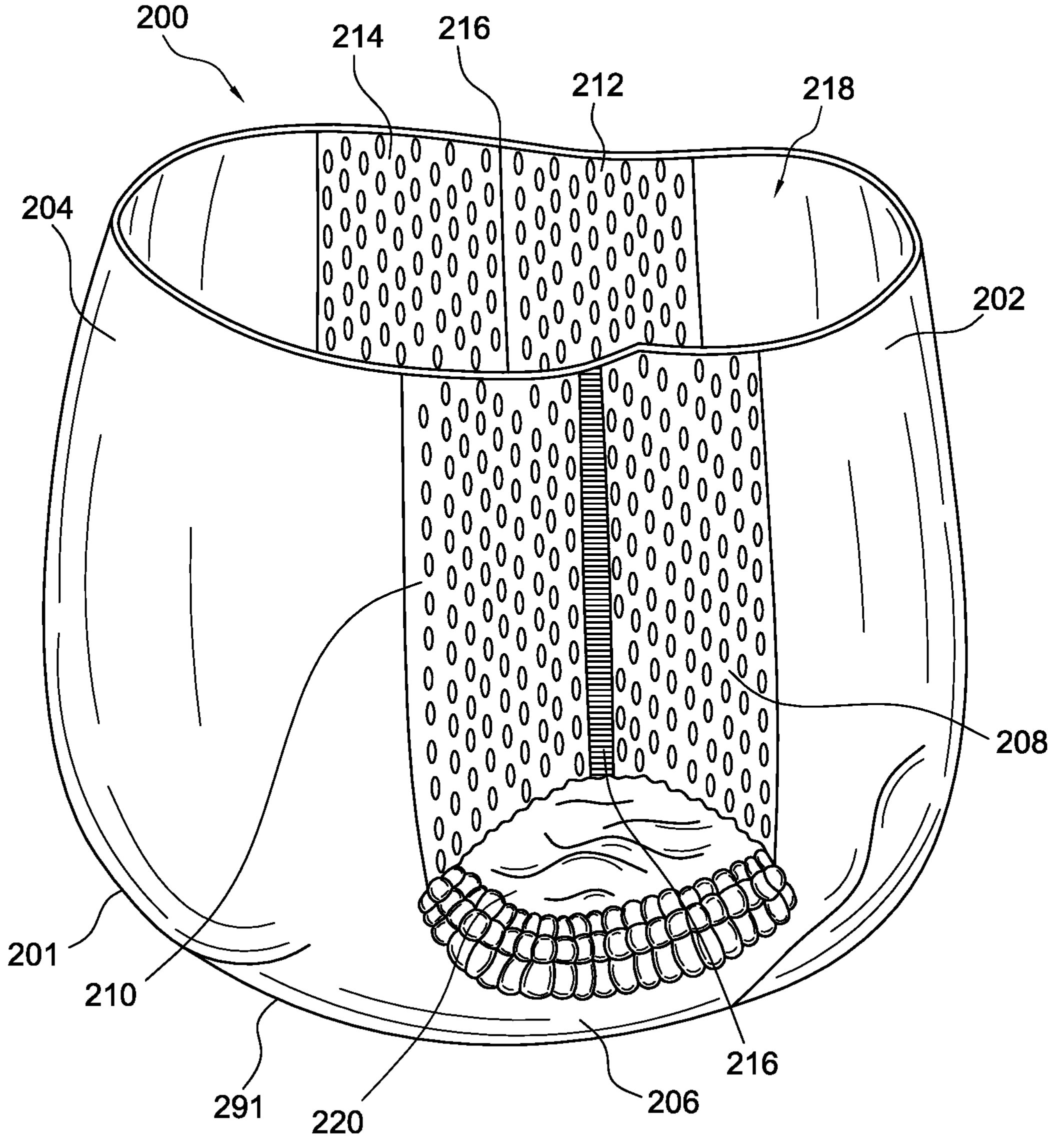
FIG. 2 is a side view of brief style absorbent article illustrating side seams.
Figure 3:
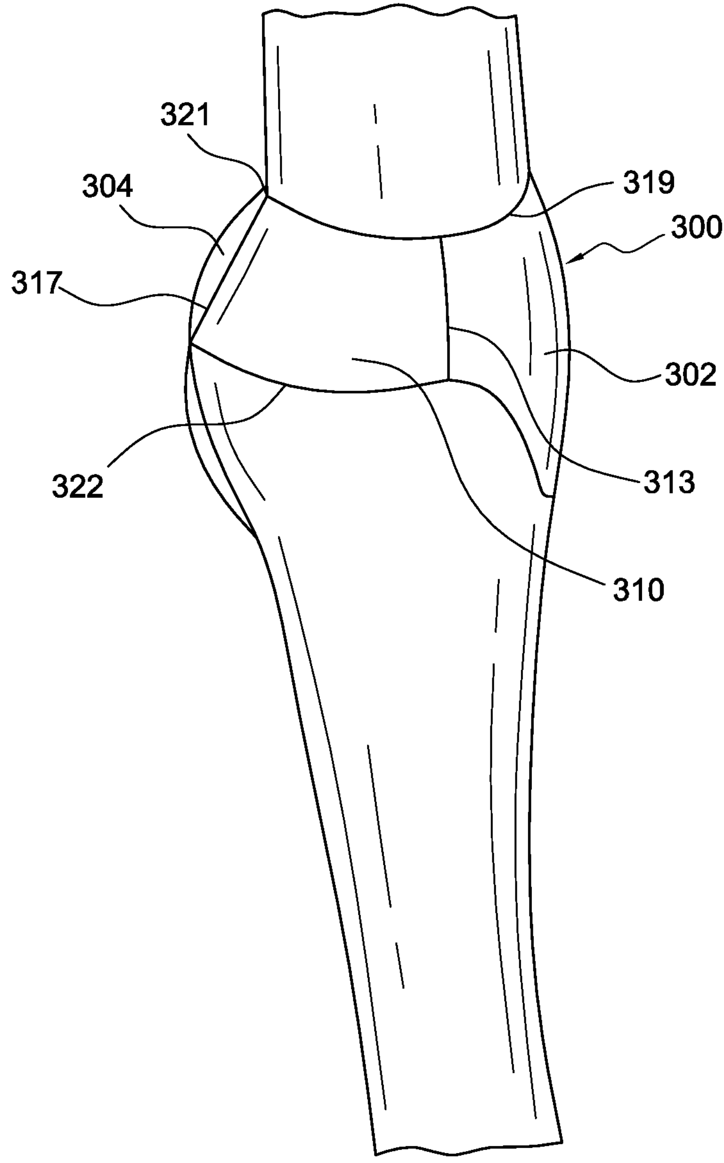
FIG. 3 is a side view of an embodiment of an absorbent article in a closed, use condition.
Figure 4:
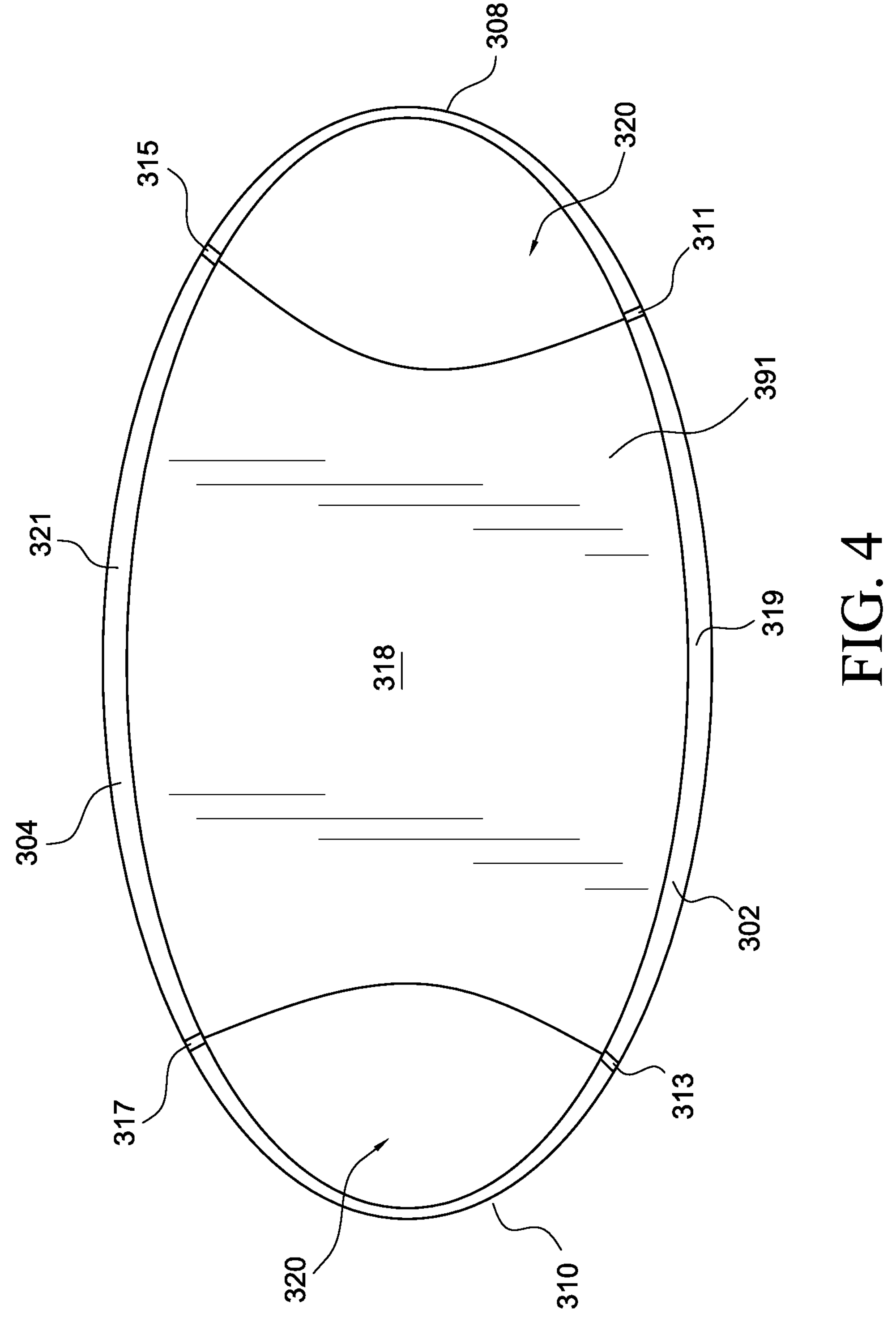
FIG. 4 is a top view of the absorbent article FIG. 3 in a closed, use condition.
Figure 5:
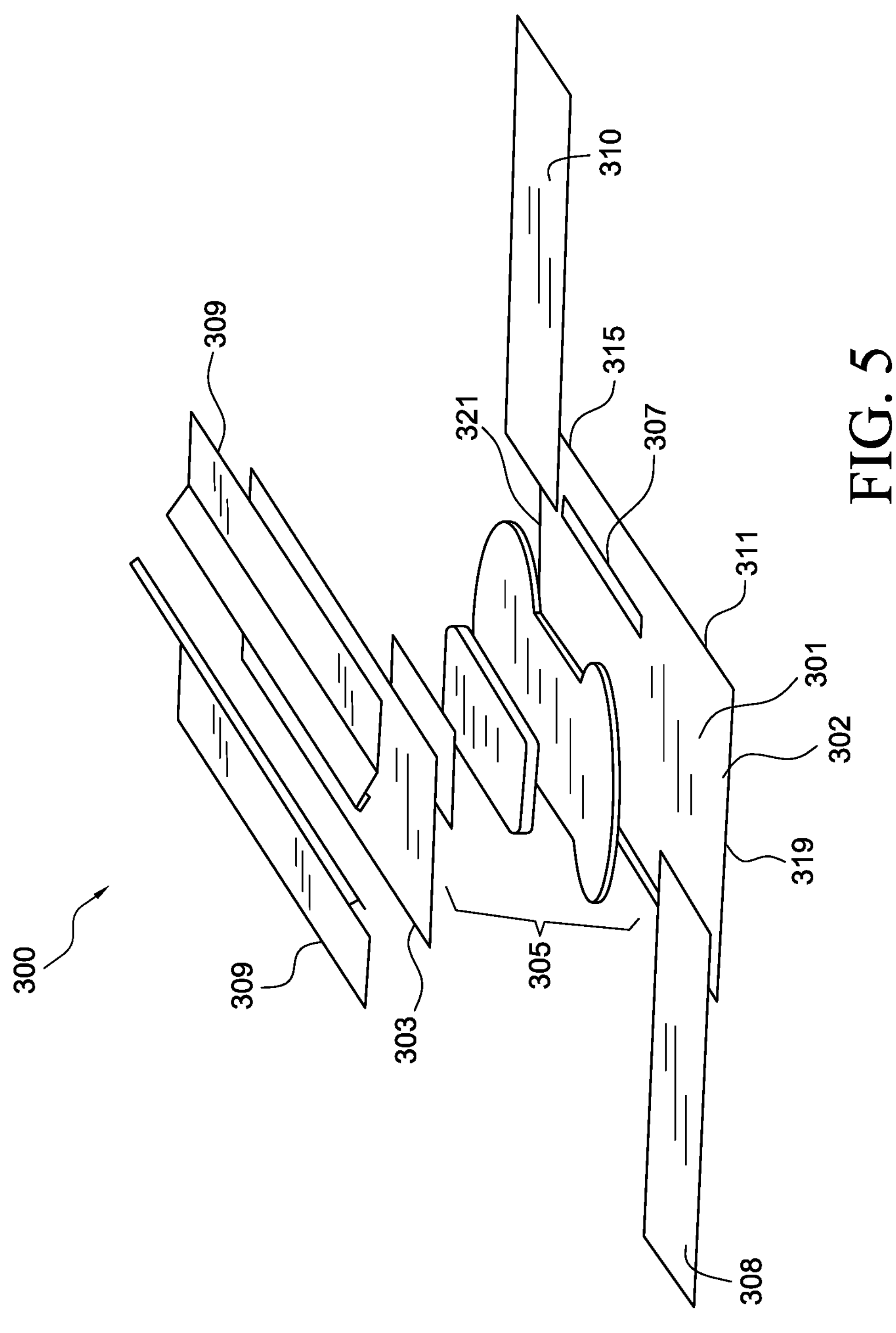
FIG. 5 is an exploded view of the absorbent article FIG. 3 in an open, flat condition.
Figure 6:
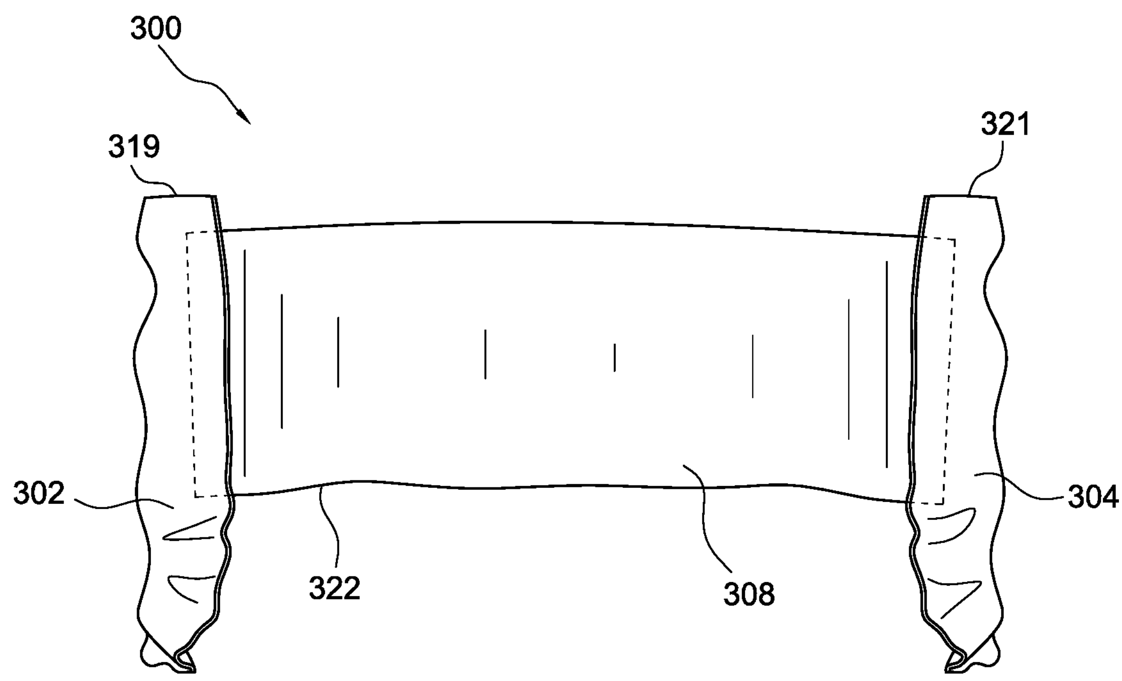
FIG. 6 is a plan view of a side panel of the absorbent article FIG. 3 in a closed, use condition.
Figure 6A:
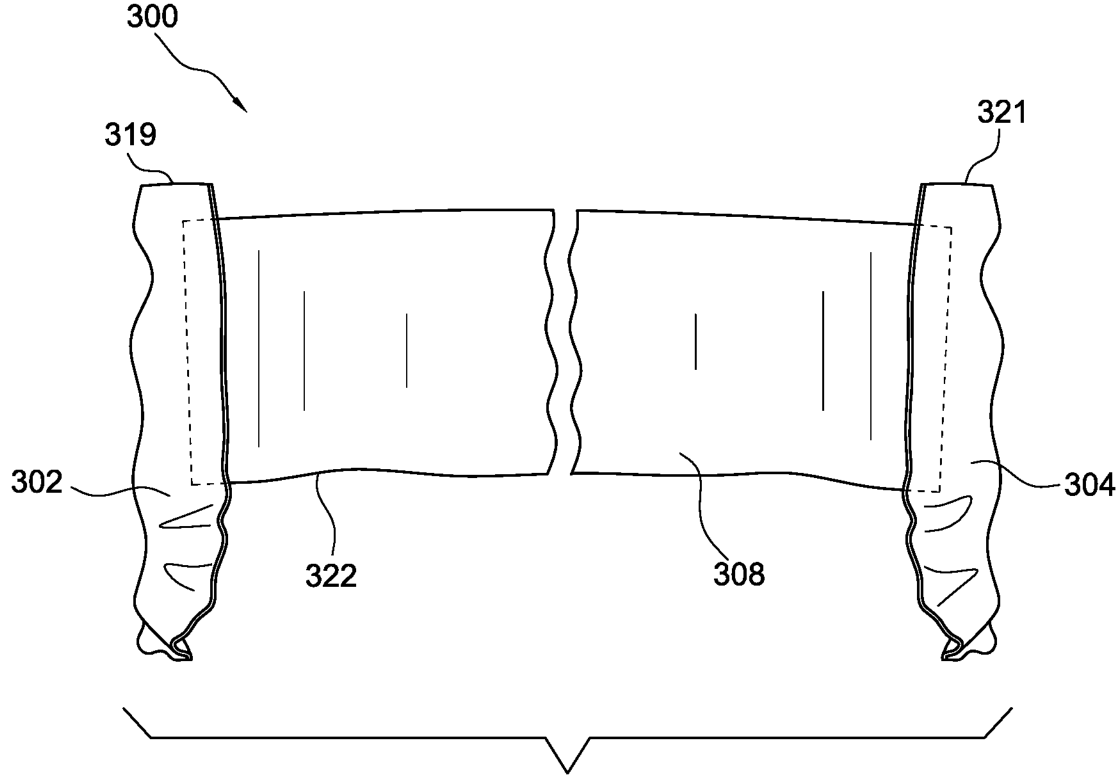
FIG. 6A is a plan view of the absorbent article of FIG. 6 after separating the side panel into two segments.

FIG. 2 illustrates a brief style disposable absorbent article 200, sometimes referred to as a training pant, pull-up, pull-on style diaper, etc. Such examples typically include a chassis 291 having front portion 202, a rear portion 204, a crotch portion 206 extending longitudinally between the front portion 202 and the rear portion 204 wherein at least a portion of the chassis 291 is configured to absorb body discharges. Extending laterally from the front and rear portions 202, 204 left and right sides are left side panels 212, 214 and right side panels 208, 210. These panels may be formed separately and joined by a seam 216 or integrally formed. Additionally, the panels may be separately formed and attached to the front and rear portions 202, 204 of the chassis 291, or they may be integrally formed with one or more layers of the front and rear portions.

Whereas diaper 100 side panels 108, 112, 112, 114 are joined by complementary fasteners 116, brief style absorbent article left front and rear side panels 212, 214 and right front and rear side panels 208, 210 may be welded, bonded or adhered together with seam 216 raw edges facing toward a wearer on an inside surface of the article or facing away from a wearer on an outside surface of the article. Once bonded, a waist opening 218 and leg openings 220 are formed.

In use, a user enters the brief style absorbent article 200 using the same techniques used to don cloth undergarments. To remove the brief style absorbent article 200, shoes are removed, clothing is lowered from about the waist and completely removed from about the ankles and feet, followed by lowering and removing the brief style absorbent article 200 in the same manner as cloth undergarments. Optionally, instead of lowering and removing the brief style absorbent article 200 a wearer or caregiver can rupture the side seams 216 or tear the side panel material, rendering the article 200 unsuitable for reuse. In some examples, the brief style absorbent article 200 may include secondary mechanical fasteners (not shown), such as hook and loop fasteners, buttons, tabs, slots, hook and eye, and other mechanical fasteners to allow the article to be used following side seam rupture. The ruptured seams, however, can cause skin abrasion and secondary fasteners can become undesirably adhered to skin, hair, clothing or other undesirable surfaces. Further, mechanical fasteners lack elasticity and add bulk to the article profile.

FIGS. 3-6 illustrate embodiments of disposable absorbent articles, more particularly, a disposable incontinence brief 300. As shown particularly in FIG. 5, the absorbent article 300 generally includes several layers: a liquid-impervious outer layer 301, an inner layer 303 substantially co-extensive with the outer layer 301 and one or more absorbent and/or distribution layers 305 interposed between the outer layer 301 and inner layer 303.

The inner layer 303 may be composed of a moisture-pervious fabric suitable to allow body discharges to pass through the inner layer 303 and be absorbed by the absorbent and/or distribution layer 305. Non-limiting examples of materials suitable to form the inner layer 303 include polypropylene, polyethylene, polyester, materials having hydrophobic properties, combinations thereof and/or the like. Additionally, the inner layer 303 can be treated with a hydrophilic finish to improve passage of fluids through to diaper layers beneath the inner layer 303. Non-limiting examples of suitable hydrophilic finishes include stearic acid, melamine-based chemicals, fluorocarbon chemicals, and silicon based chemicals.

The outer layer 301, which faces away from the wearer, is composed of a liquid-impervious fabric. Accordingly, the outer layer 301 may be made of any material suitable to minimize or prevent biomatter from escaping the absorbent article 300. Non-limiting examples of suitable materials for the outer layer 301 include polyethylene or other polymer materials and may be breathable.

In some embodiments, the absorbent article 300 can include a set of leak guards 307 and/or a set of leg cuffs 309.

Embodiments of the absorbent article include a chassis 391 having a front portion 302, a rear portion 304, a crotch portion 306 connected there between, and a plurality of laterally extending side panels corresponding with a wearer's hip region. The front portion 302 defines a pair of laterally opposed side edges 311, 313 and a longitudinally opposed waist edge 319. The rear portion 304 defines a pair of laterally opposed side edges 315, 317 and longitudinally opposed waist edge 321. The front portion 302 and the rear portion 304 encompass a single layer of material, or may be constructed from a laminate material, elastomeric laminates, films, etc. or may have applied or attached elastic fibers. The plurality of side panels extend laterally outward from and between each opposed side edge 311, 313, 315, 317 of the front and rear portions 302, 304.

In certain embodiments, the side panels 308, 310 may be attached to the front and rear portions 302, 304 by welding, bonding, adhesive, or sewing, or other suitable techniques. In some embodiments, the side panels 308, 310 may be attached in between the outer and inner layers 301, 303. In other embodiments, the side panels 308, 310 may be attached to the outer layer 301. In a still further embodiment, the side panels 308, 310 may be attached to the inner layer 303. In a further embodiment, the side panels 308, 310 may be attached to both the outer and inner layers 301, 303.

Left and right leg openings 320 are defined by bottom edges 322 of the side panels 308, 310 and the longitudinal edge portions of the front, rear portions 311, 315, 313, 317. In accordance with the embodiments of FIGS. 3-6, the plurality of side panels includes two side panels. The first side panel 308 which when joined to the left side front portion longitudinal edge 311 and left side rear portion longitudinal edge 315 forms a left leg opening 320. The second side panel 310, which when joined to the right side front portion longitudinal edge 313 and the right side rear portion longitudinal edge 317 forms a right leg opening 320. In this manner, the respective waist regions of the front and rear portions 319, 321, together with the side portions 308, 310 form a complete waist opening 318.

In accordance with certain embodiments, including at least the embodiment illustrated in FIGS. 3-6, the side panels 308, 310 may be constructed from cohesive material. Cohesive material may be extensible and elastomeric. In accordance with embodiments, the cohesive material may expand laterally. In addition, the cohesive material may be such that after extension, the cohesive material will contract to its original lateral dimension, or in alternative embodiments to within 50% of its original lateral dimension. Owing to the expansion and contraction properties, the cohesive side panels 308, 310 will provide consistent support and maintain compression around the waist and/or legs of the user. Accordingly, the act of pulling the absorbent article 300 and the corresponding extension of the waist band opening 318 and side panels 308, 310 up over the wearer's buttocks and hips followed by releasing the waist band opening 318 (and side panels 308, 310) will not substantially detract from the intended fit of the absorbent article 300 around a user's waist region.

A wide variety of cohesive materials may be used to form the cohesive refastenable features discussed herein. For example, the side portions of the absorbent article may be formed, at least in part from cohesive material. Embodiments of the side portions will demonstrate high resistance to shear forces in use, but significantly less resistance to peel forces in use. For example, the cohesive materials may be chosen to demonstrate resistance to shear forces greater than 10 N, preferably greater than 30 N. Similarly the resistance to peel forces might range from about 0.5 N to about 25 N, or could range from about 0.5 N to about 15 N, and could range from about 0.7 N to about 10 N. The cohesive materials may be chosen such that the cohesive material may be refastened at least three or more times before product disposal.

Figure 9:
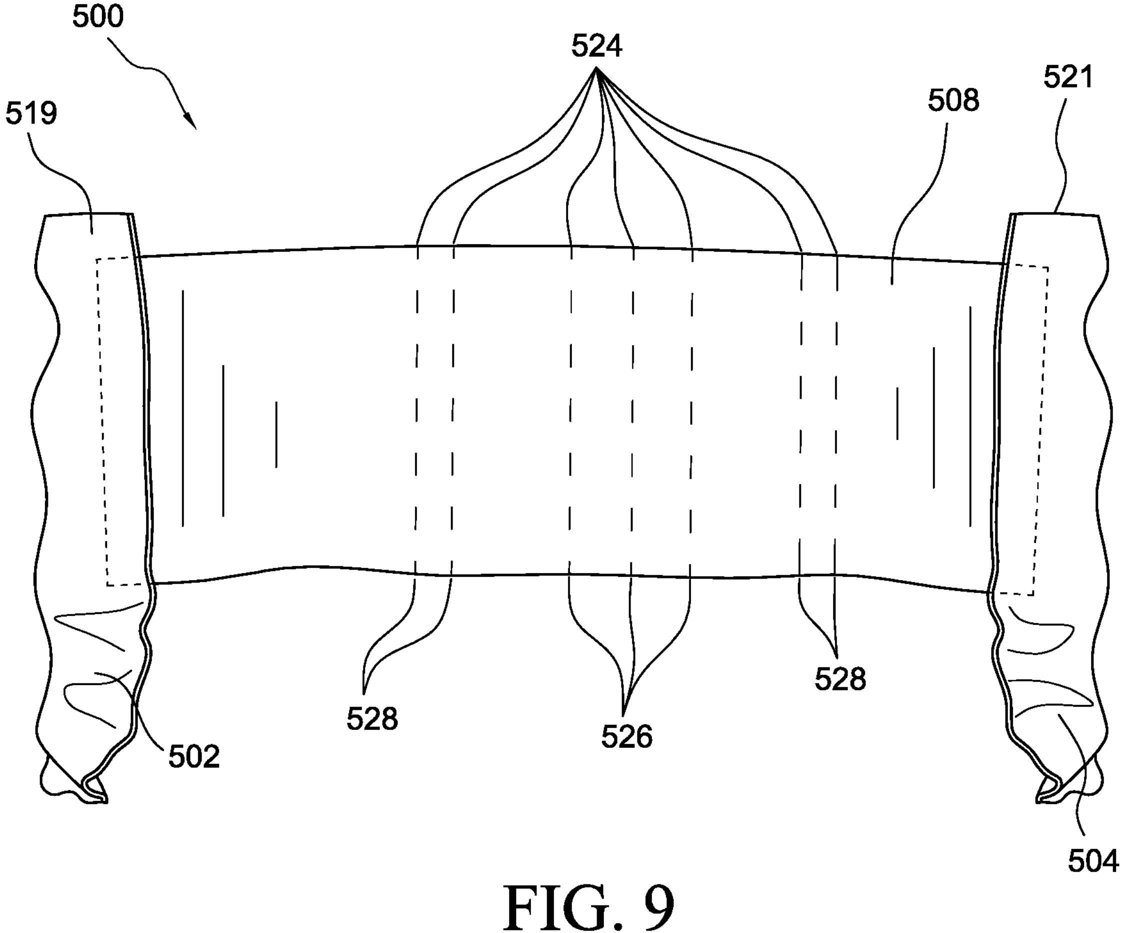
FIG. 9 is a plan view of the side panel of the absorbent article FIG. 8 in a closed, use condition.
Figure 10:
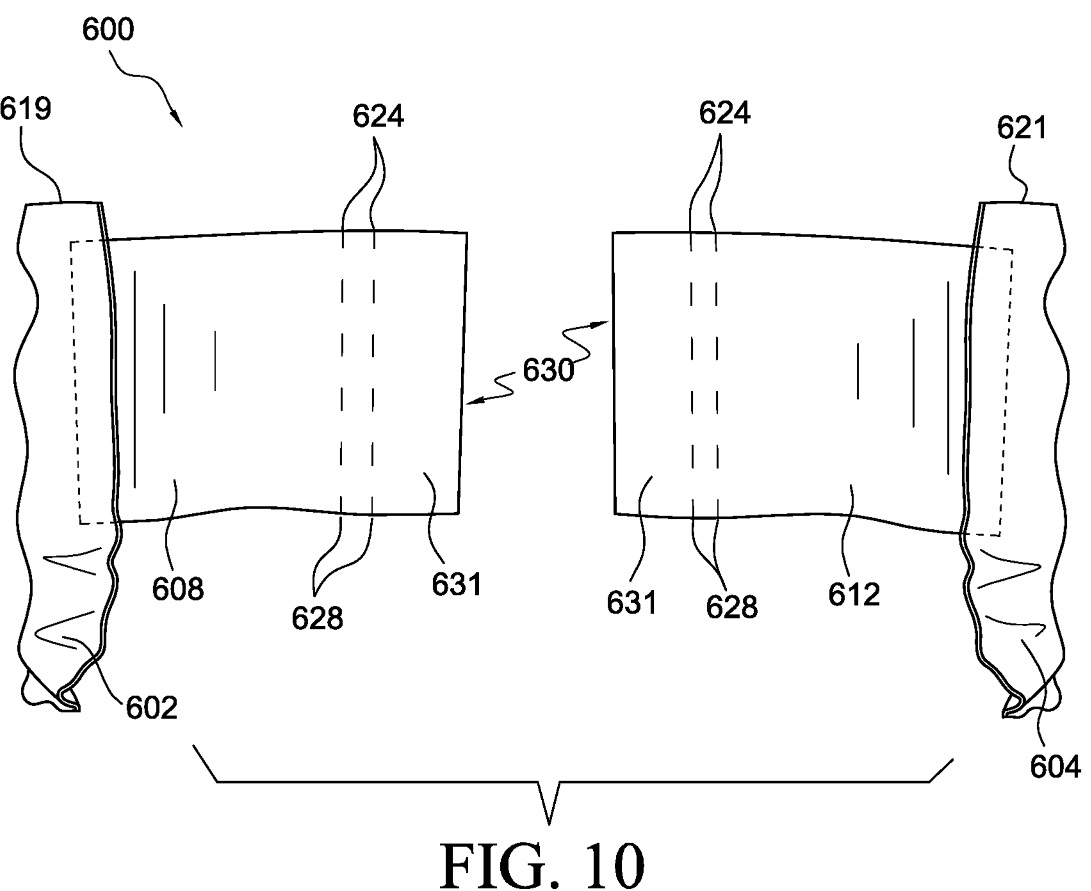
FIG. 10 is a plan view of the absorbent article of FIGS. 8-9 after separating the side panel into two segments.
Figure 11:
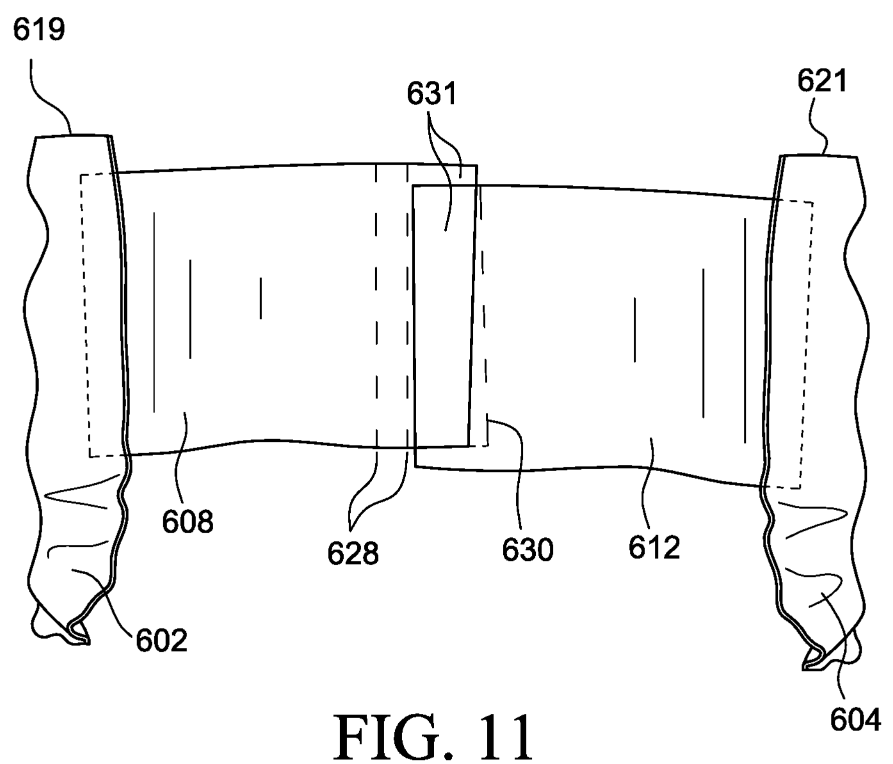
FIG. 11 is a plan view of the absorbent article of FIG. 10 in which the side panels have been rejoined.
Figure 12:
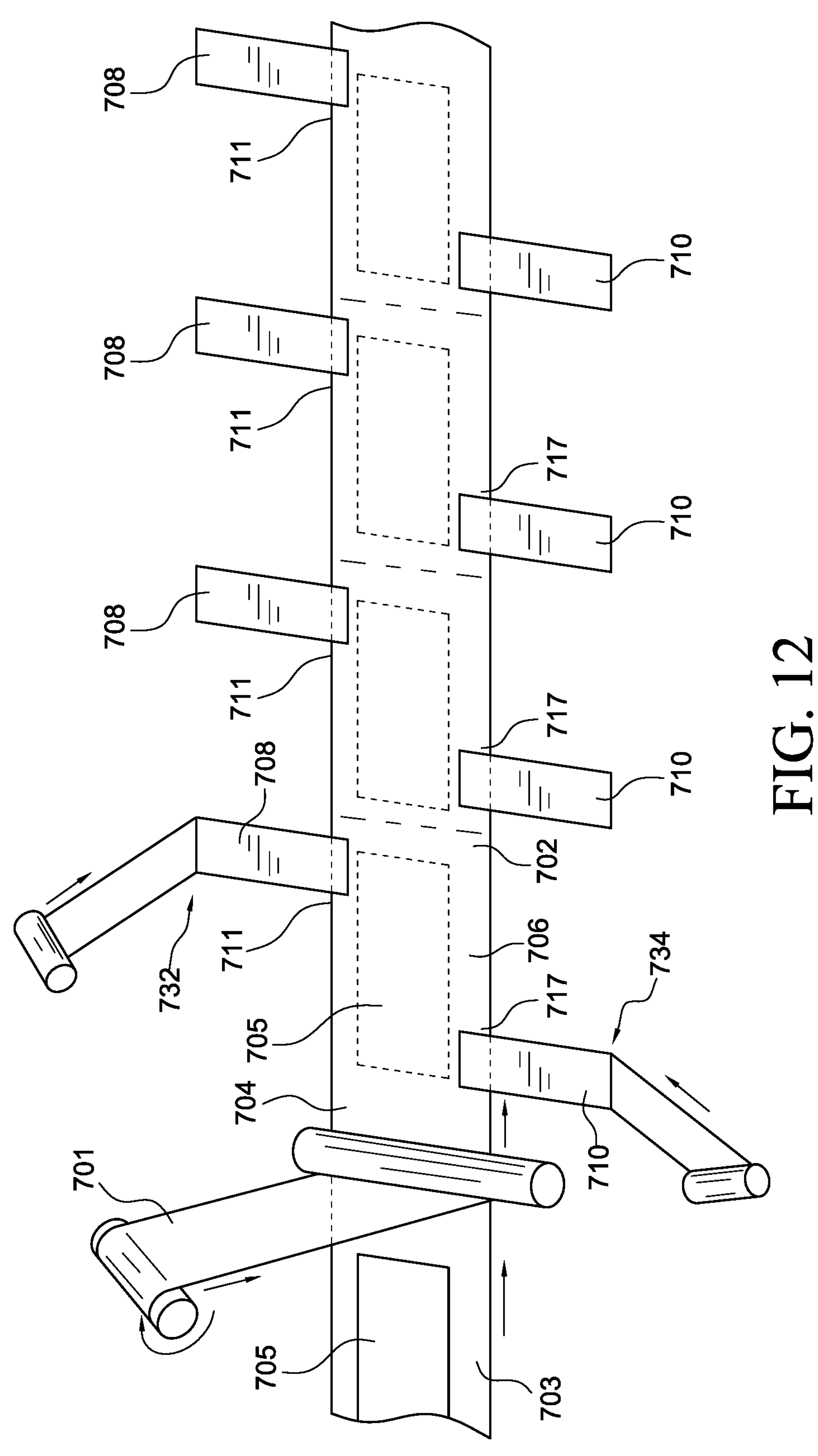
FIG. 12 is a representative diagram illustrating steps in an embodiment of a manufacturing process for manufacturing embodiments of an absorbent article.
Figure 13:
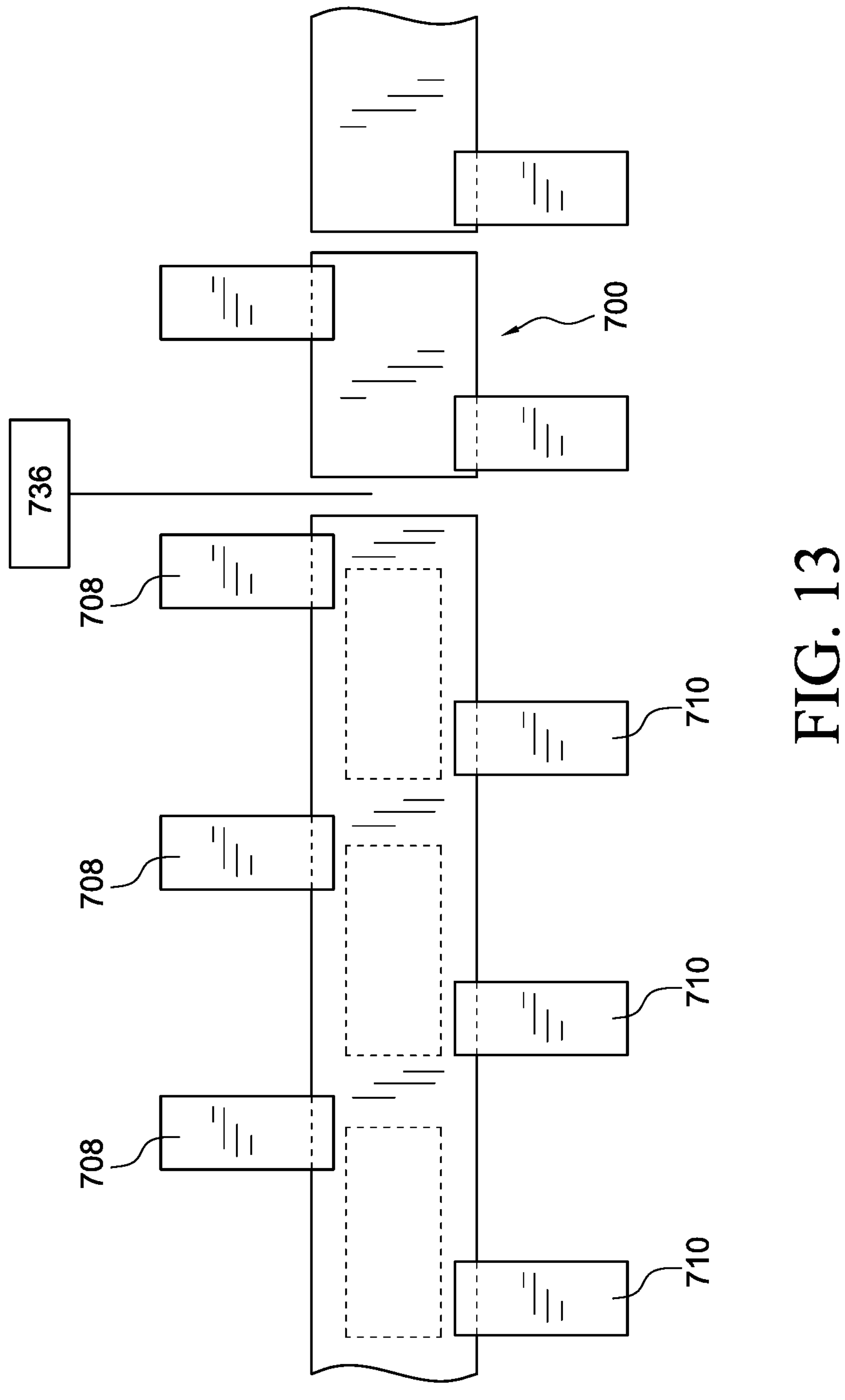
FIG. 13 is a representative diagram illustrating further steps in the embodiment of a manufacturing process of FIG. 12.
Figures 14, 15, 16, 17:
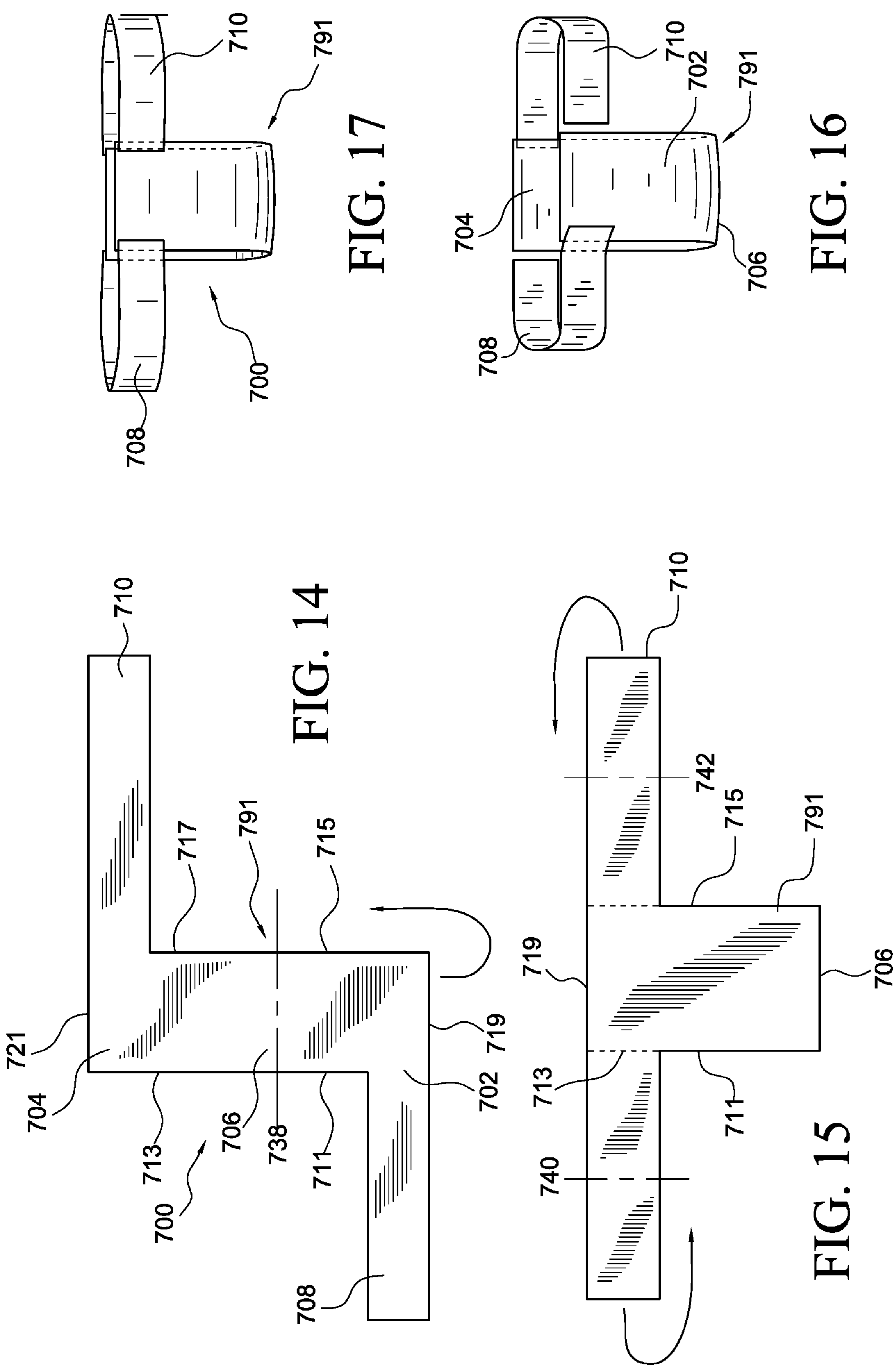
FIG. 14 is a plan view of an embodiment of an absorbent article in an open, flat condition.
FIG. 15 is a plan view of a further embodiment of an absorbent article in an open, flat condition.
FIG. 16 is a perspective view of the embodiment of FIG. 14.
FIG. 17 is a perspective view of the embodiment of FIG. 15.

Cohesive materials may be pressure sensitive. In the embodiment illustrated in FIGS. 8-9, a first side panel 508 is provided on a first side of the absorbent article, and a second side panel 510 is provided on a second side of the absorbent article. The first side panel 508 connects a first front side edge 511 with a first rear side edge 515. The second side panel 510 similarly connects a second front side edge with a second rear side edge 517. Once the article 500 is pulled over the hips of the wearer, the first and second side panels 508, 510 may be torn, and overlapped to refasten the side portions. For example, as illustrated in FIG. 10, once the side panels 508, 510 have been torn, instead of two side panels as initially provided, the absorbent article 600 now includes four side panels 608, 612, 610, 614. The left side now includes first (front) and third side (rear) panels 608, 612 while the right side now includes second (front) and fourth (rear) side panels 610, 614. These corresponding side panels may be overlapped at an attachment area 631 and rejoined as shown in FIG. 11, allowing the absorbent article to be re-donned or to be inspected and reconnected.

There are multiple benefits to having side portions constructed from cohesive materials. By way of example, firstly, by easily tearing the cohesive material first and second side portions 508, 510, the user can remove the absorbent article 500 without having to remove lower clothing from about the ankles and feet, for example when in a public restroom setting. Secondly, as cohesive material has a soft touch, the act of tearing the cohesive material will elicit minimal noise, thus helping the wearer to maintain dignity in public restroom settings. Thirdly, tearable cohesive material allows the wearer to customize the fit of the absorbent article 500 and achieve a more snug fit by overlapping segments of the side portions. Fourthly, since cohesive materials are self-adhering, they will not stick to clothing, hair or skin and consequently will not become a skin irritant or become soiled by intermittent contact with other surfaces, such as skin, hair or clothing.

Figure 7:
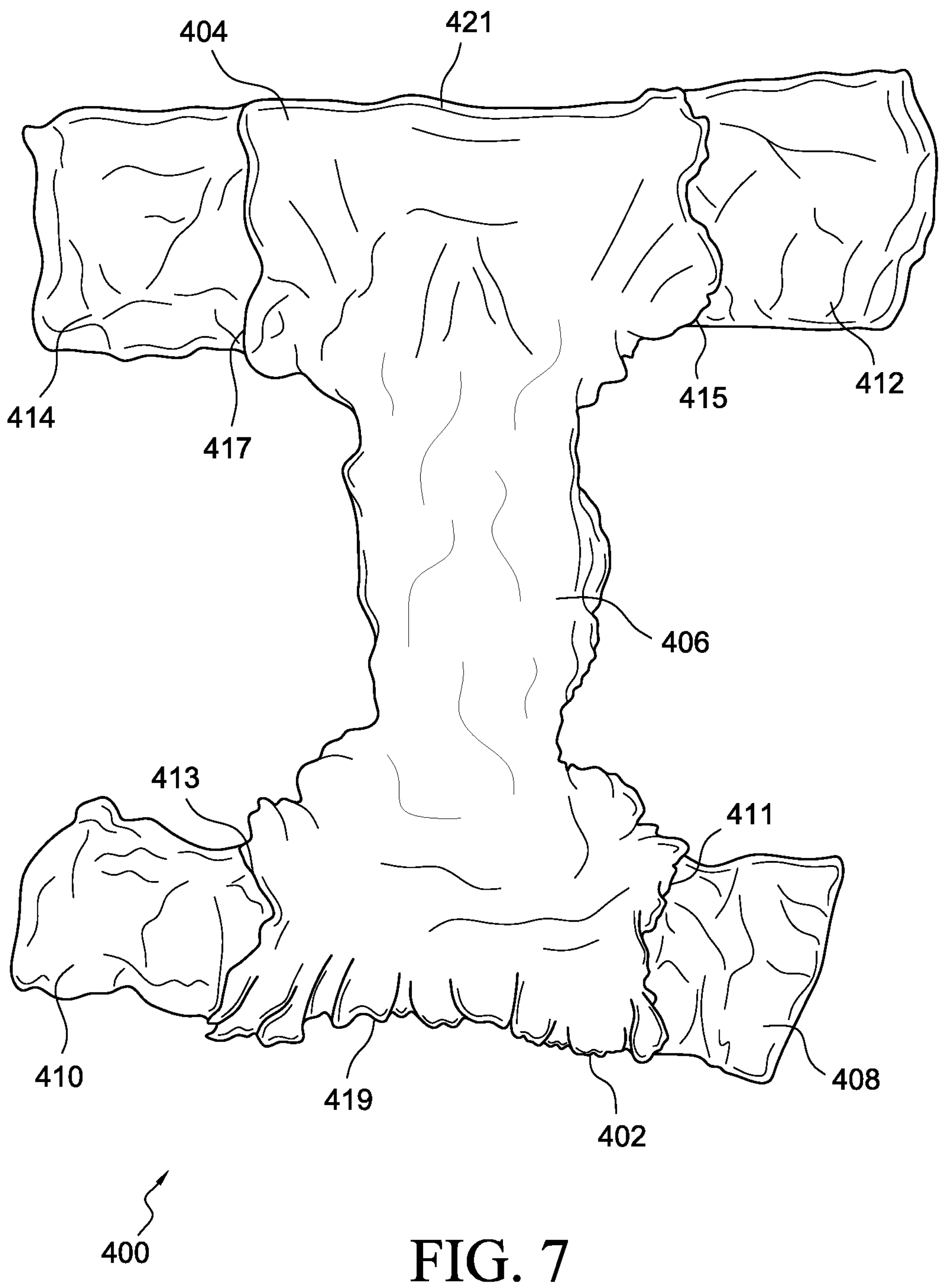
FIG. 7 is a plan view of an embodiment of an absorbent article in an open, flat condition.

In accordance with the embodiment of FIG. 7, the plurality of side panels may include four side panels 408, 410, 412, 414. The first side panel 408, joined to the left side front portion longitudinal edge 411; a second side panel 410, joined to the right side front portion longitudinal edge 413; a third side panel 412, joined to the left side rear portion longitudinal edge 415; and a fourth side panel 414, joined to the right side rear portion longitudinal edge 417.

To secure the side panels 408, 410, 412, 414 to form a waist opening 418 and leg openings 420, the cohesive material side panels 408, 410, 412, 414 are attached to one another such that first and third (front and rear) side panels 408, 412 join together and second and fourth (front and rear) side panels 410, 414 join together. The first and third 408, 412 and second and fourth 410, 414 side panels, respectively may overlap, or join inside face to inside face or outside face to outside face, or in any other technique suitable to cohesive joining cohesive material.

In accordance with the various embodiments, the absorbent article may include aesthetically pleasing color features so as to suggest that the article resembles the color features of traditional undergarments. By way of non-limiting example, the article may be buff colored, gray, or black, or include a multi-colored pattern, designs or indicia.

In accordance with the various embodiments, side panels constructed from a stretchable, cohesive material allows for a single article to fit a greater number size range of wearers. This reduces waste as there is a reduction in the amount of machinery needed to build multiple size accommodating articles, as well as less change over from product size to product size, thereby increasing efficiency in the manufacturing process.

Figure 8:
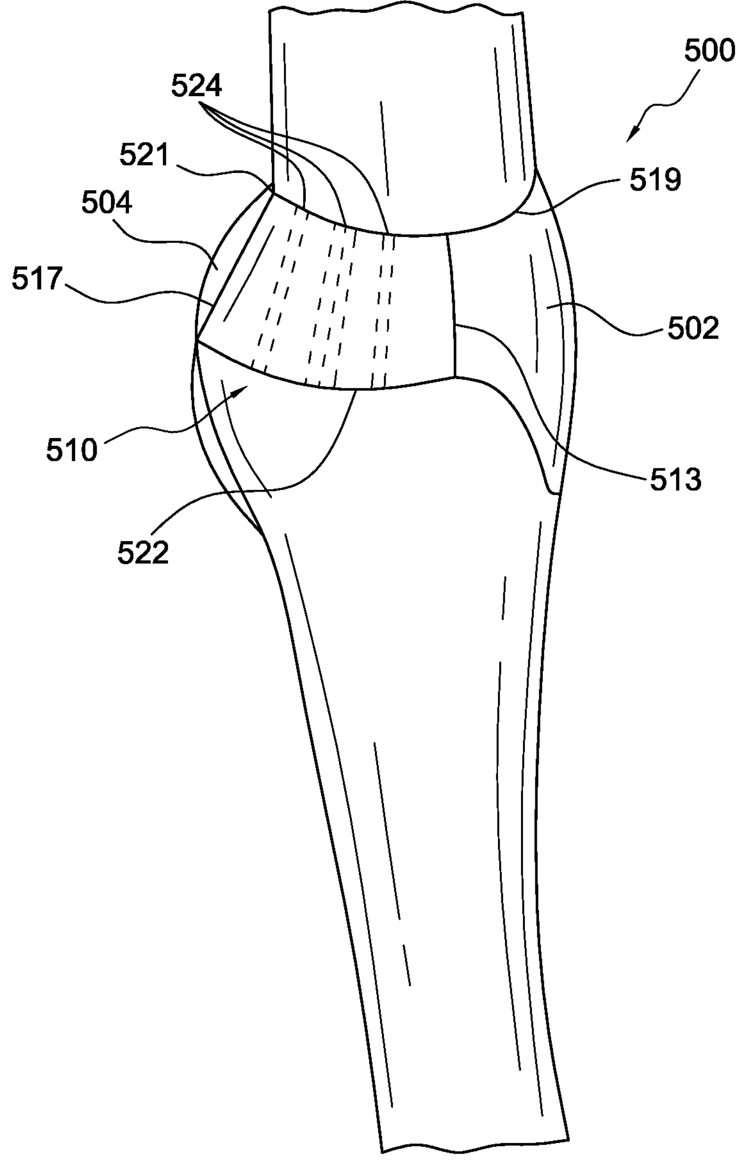
FIG. 8 is a side view of an embodiment of an absorbent article in a closed, use condition.

In an embodiment, the absorbent article may be customized to improve the fit around a wear's torso or to improve comfort. As illustrated in FIGS. 8 and 9, the side panels 508, 510 may include a sizing indicator 524. Non limiting sizing indicator 524 examples include lines, colors, symbols, graphics, letters, words, or other indicators. In another embodiment, the sizing indicator 524 may include frangible or perforated sections in the side portions 508, 510. In accordance with the various embodiments, sizing indicators can provide visual signals to a wearer offering suggested tear points 526 in the cohesive material.

In this way, after donning a brief style absorbent article 500, a wearer can adjust the fit of the absorbent article by tearing each of the first and second side panels 508, 510 at corresponding sizing indicator tear points 526. In use, a user tears side panel 508 along the sizing indicator 526. Instead of two side panels as initially provided, the absorbent article 600 now includes four side panels 608, 612, 610, 614. The left side now includes first and third (front and rear) side panels 608, 612 while the right side now includes second and fourth (front and rear) side panels 610, 614. In accordance with the embodiment of FIGS. 10-11, by tearing 630 the side panels 608, 610 at corresponding sizing indicator 624 positions 626, a symmetrical fit of the absorbent article 600 around the wearer's body will be maintained. In this way, the torn first and second side panels 608, 610 will extend laterally by substantially the same distance. Similarly, newly formed third and fourth side panels 612, 614 will extend laterally by substantially the same distance. Accordingly, when cohesively rejoining the first and third side panels 608, 612 and the second and fourth side panels 610, 614, further sizing indicators 624 suggest zones for reattachment or landing 628. Maintaining symmetry of the absorbent article 600 around a wearer's body is critical to reducing sagging, bagging and leaking of an absorbent article 600 and ensuring a proper fit has been achieved.

In an alternative embodiment, a wearer may want to only tear one of the side panels, for example, following a surgical procedure to the wearer's waist or hip region. In accordance with this embodiment, the absorbent article is sized to extend up and over any surgical dressings. To improve the fit of the absorbent article, the wearer may only tear one side portion so as to reduce any sagging, bagging or leaking on the side opposite the surgical dressing. Said differently, the cohesive side panel extending over a surgical site is extensible over the surgical dressing on say, for example the left hip, but the right hip area does not include a surgical dressing, and thus the right side panel may be looser fitting. To improve the fit of the absorbent article relative to the right side, the wearer will tear the cohesive material side portion extending along the right side of the article, overlap the now torn side portions and improve the fit about the waist region. The untorn left cohesive material side panel does not include any raw edges or seams which could cause surgical site irritation.

While a brief style absorbent article is depicted, those skilled in the art will recognize that bikini, boxer, boxer brief and other styles of absorbent articles (for example, diapers and training pants) can be implemented without departing from the scope of the embodiments disclosed herein.

FIGS. 12-17 illustrate embodiments of a method for manufacturing an absorbent article 700 in accordance with the embodiments of FIGS. 3-6 and 8-11. Embodiments of the manufacturing method may include the following steps: (1) providing a layup for an absorbent article including a chassis 791 having a front portion 702, a rear portion 704 and a crotch portion 706 extending there between. The absorbent article layup further includes providing a length of inner sheet 703 material and cut sections of absorbent and/or distribution layer 705 material in a first direction; (2) unwinding a continuous length of the outer sheet material 701 in a second direction; (3) providing a continuous length of side panel material in a third direction transverse to the first and second directions and cutting the side panel material into discreet lengths for placement along the front portion first longitudinal edge 711. This first cut piece of side portion material forms the first side panel 708 by feeding in a third direction, transverse to the first and second directions, a continuous length of side portion material through a slip and cut 732 (also known to those skilled in the art as cut and place) which can be performed with a cutting unit followed by a placing unit—as driven by either mechanical cam or servo motor unit, thereby providing an intermittent length of side portion material along a first side, first position of the absorbent article layup. The slip/cut applicator may also require a vacuum in order to hold the side portion within the unit until severed, accelerated and welded, bonded or adhered in place to the backsheet. In a fourth step, a second continuous length of side portion material is fed into the system in a fourth direction, different from the third direction and transverse to the first and second directions, a continuous length of side portion material through a slip and cut 734, thereby providing an intermittent length of second side panel 710 material along a second side longitudinal edge 717, second position of the absorbent article layup. In a fifth step, a cutoff and spacing unit 736 severs and spaces the layup into discreet absorbent articles 700. In a sixth step, a folding machine folds the absorbent article chassis 791 in half along an x axis 738; the front and rear portion waist portions 702, 704 are now aligned and left and right side panels 708, 710 extend along the x axis from their respective left side front portion 702 at 711 and right side rear portion 704 at 717. In a seventh step, the left side panel 708 is folded in half along they axis 740 and joined to the left side rear portion 713 by welding, bonding or adhering. Similarly, the right side panel 710 is folded in half along they axis 742 and joined to the right side front portion 715 by welding, bonding or adhering. The side panels 708, 710 may be affixed to either the inner layer 703 or the outer layer 701.

In an alternative embodiment, the side panels 708, 710 may be affixed between the inner layer 703 and outer layer 710.

Figure 18:
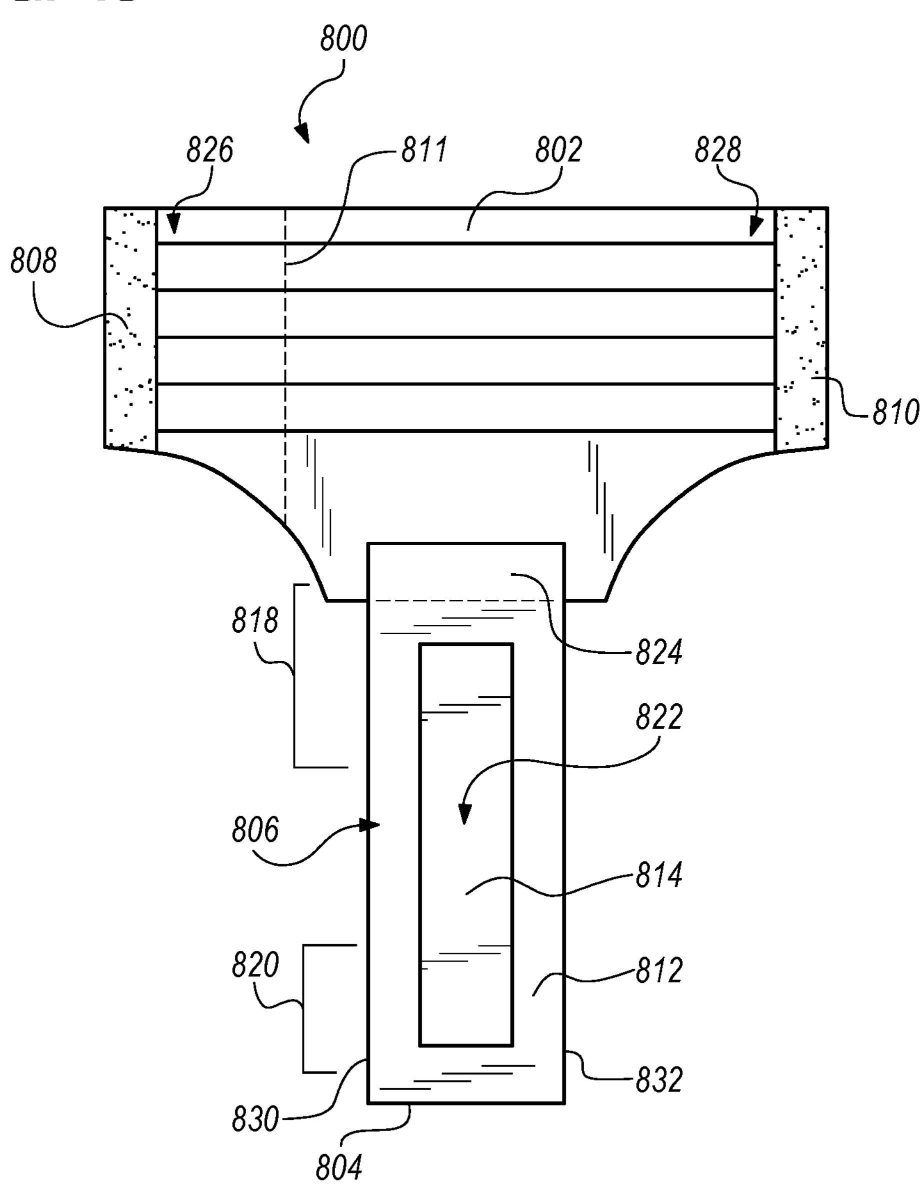
FIG. 18 is a plan view of an embodiment of a protective underwear in an open, flat condition.
Figure 19:
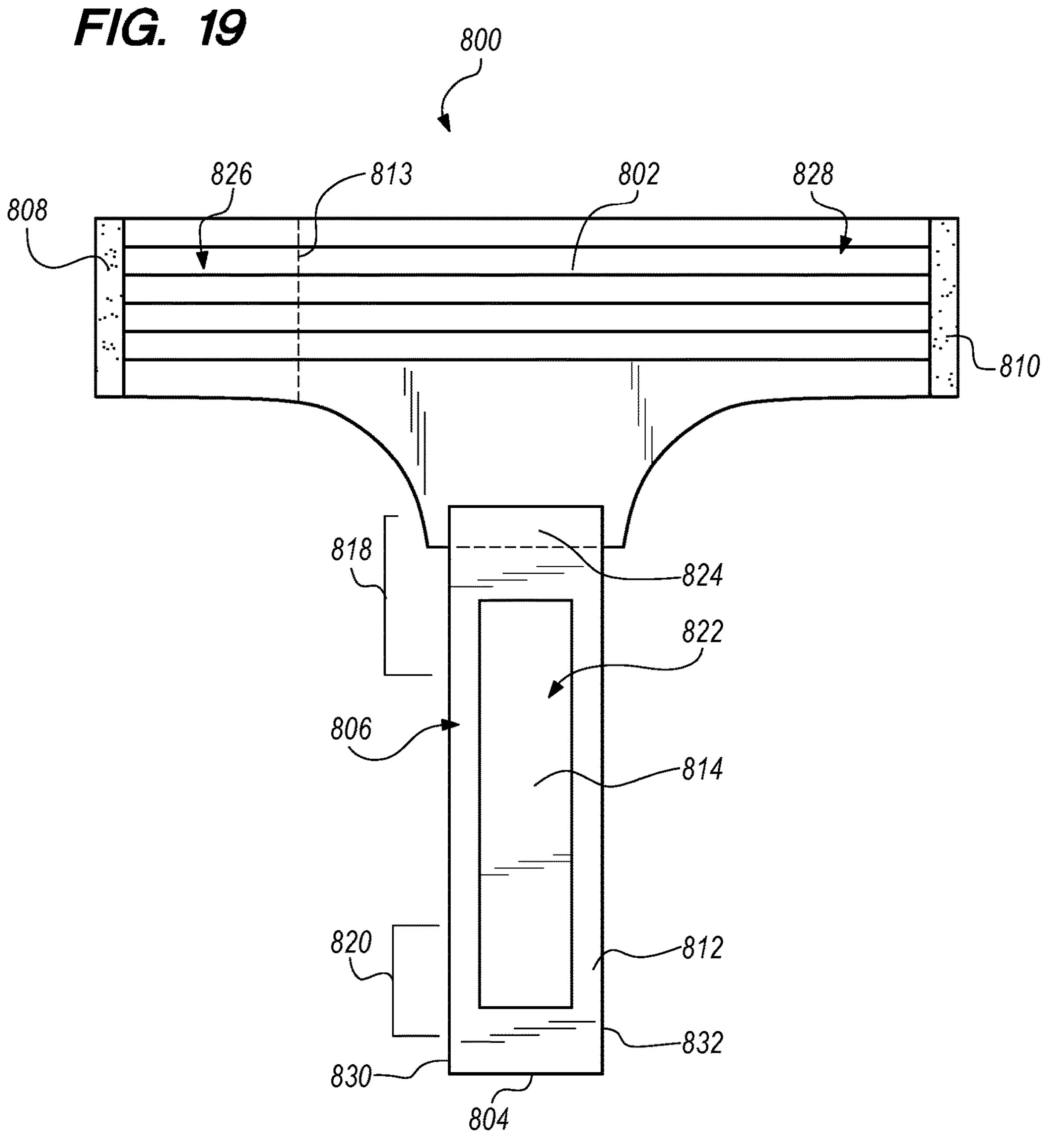
FIG. 19 is a plan view of an embodiment of a protective underwear in an open, flat condition.

Referring to FIGS. 18-19, in one embodiment, a protective underwear 800, which may be interchangeable with a brief, in a substantially flat un-contracted state, having a reduced component configuration that accommodates multiple sized brief wearers. The protective underwear 800 has a rear portion 802 and a front portion 804. The protective underwear 800 further comprises a chassis 806, a first securement portion 808, and a second securement portion 810. Although not shown in this figure, the protective underwear 800 may include a set of leak guards and/or a set of leg cuffs both known to those of ordinary skill in the art. In this embodiment there are two body securement portions/panels comprising the first securement portion 808 and the second securement portion 810. It should be noted that two securement portions are used in this embodiment; however, it should be recognized that other embodiments may be configured with more or fewer securement portions/panels.

The protective underwear 800 generally consists of several layers, including an inner layer 812, an absorbent layer 814, and a liquid impervious outer layer 816. The inner layer 812 faces a wearer and contacts the skin of the wearer when the protective underwear 800 is secured to the wearer. The inner layer 812 may be composed of a moisture-pervious fabric suitable to allow bodily discharge to pass through the inner layer 812 and be absorbed by the absorbent layer 814. Non-limiting examples of materials suitable to form the inner layer include polypropylene, polyethylene, polyester, materials having hydrophobic properties, combinations thereof and/or the like.

First securement portion 808 and second securement portion 810 are coupled to and may extend from the rear portion 802. The rear portion 802 is generally positioned against the back of the user and covers the buttocks of the user. The chassis 806 is generally positioned against the front of the user. The first securement portion 808 and the second securement portion 810 wrap around a wearer's waist from back to front. In this manner, first securement portion 808 and second securement portion 810 can be coupled to the chassis 806, to couple the chassis 806, which comprises the front portion 804, to the rear portion 802.

The protective underwear 800 includes the chassis 806. The chassis 806 has a substantially rectangular outer perimeter including a length extending in a longitudinal direction from the back to the front of a user and a width extending in a lateral direction substantially perpendicular to the length between first and second longitudinal edges. The chassis 806 comprises a first portion 818, a second portion 820 and a crotch portion 822 extending between the first and second portion 818, 820. Further, the chassis 806 comprises a portion of the absorbent layer 814. The protective underwear 800 in this illustration of FIG. 18 is shown with the portion of the protective underwear 800 that contacts the wearer shown facing the viewer. The chassis 806 is that portion of the protective underwear 800 which, when the protective underwear is worn, is generally positioned between the legs of the wearer. In other embodiments, there may be portions of the chassis 806 that are shaped and/or removed, such as in the crotch region 822, for example, resulting in a narrower crotch region portion to provide a contoured fit between the legs. Still other embodiments have different shaped chassis 806, such as hourglass shapes, and the like. The chassis 806 has a chassis width and a chassis length. The chassis 806 width is a common width across all article sizes that accommodate a plurality of body sizes. In other words, one chassis width is used for different sized protective underwear articles while still accommodating different wearer's body sizes.

The first portion 818 of the chassis 806 is coupled to an attachment portion 824 of the rear portion 802, forming a T-shaped protective underwear. The rear portion 802 includes the first securement portion 808 operatively coupled to a first side portion 826 of the rear portion, the first securement portion 808 having a width extending in a lateral direction from the first side portion 826 of the rear portion. The rear portion 802 includes the second securement portion 810, the second securement portion 810 having a width extending in a lateral direction from a second side portion 828 of the rear portion. Further, the first and second securement portions 808, 810 and rear portion 802 comprise elastic material. These elastic materials may be found in sections on the first and second securement portions 808, 810, or they may be coextensive with entirety of the rear portion 802. The elastic material may be made from, for example, spandex, rubber, etc. It will be appreciated by those in the art that a rear portion 802 comprising elastic material can accommodate numerous sizes of people. For example, having a size medium protective underwear may accommodate some wearer's that typically wear a small or large due to the elasticity of the first and second securement portions 808, 810. Further, the rear portion 802 may vary in latitudinal widths to accommodate all wearers, such as a first width 811 (FIG. 18) or a second width 813 (FIG. 19). The first width 811 is a taller latitudinal width to accommodate users needing a larger size, and the second width 813 is a typical, normal width.

The first and second securement portions 808, 810 may couple to the second portion 820 of the chassis 806 by using mechanical fastening elements (hook and loop, snaps) or cohesive material, which allows the protective underwear 800 to be secured around a user's waist. The second portion 820 of the chassis 806 may have a first chassis receiving portion 830 and a second chassis receiving portion 832 that can also be any mechanical fastening element or cohesive material to function in tandem with the first and second securement portions 808, 810. The first and second chassis receiving portions 830, 832, located on the side not in contact with a user, receive and couple to the first and the second securement portions 808, 810 that are coupled to the rear portion 802. It would be understood by anyone in the art that the protective underwear 800 may be removably attachable. Further, it will be appreciated that the first and second securement portions 808, 810 may be refastened by a user in order to find a proper, custom fit. For example, if the initial fit is improper, a user can detach the first and/or second securement portions from the first and/or second chassis receiving portions 830, 832 and reattach in a different position until the user has a proper fit.

Figure 20:
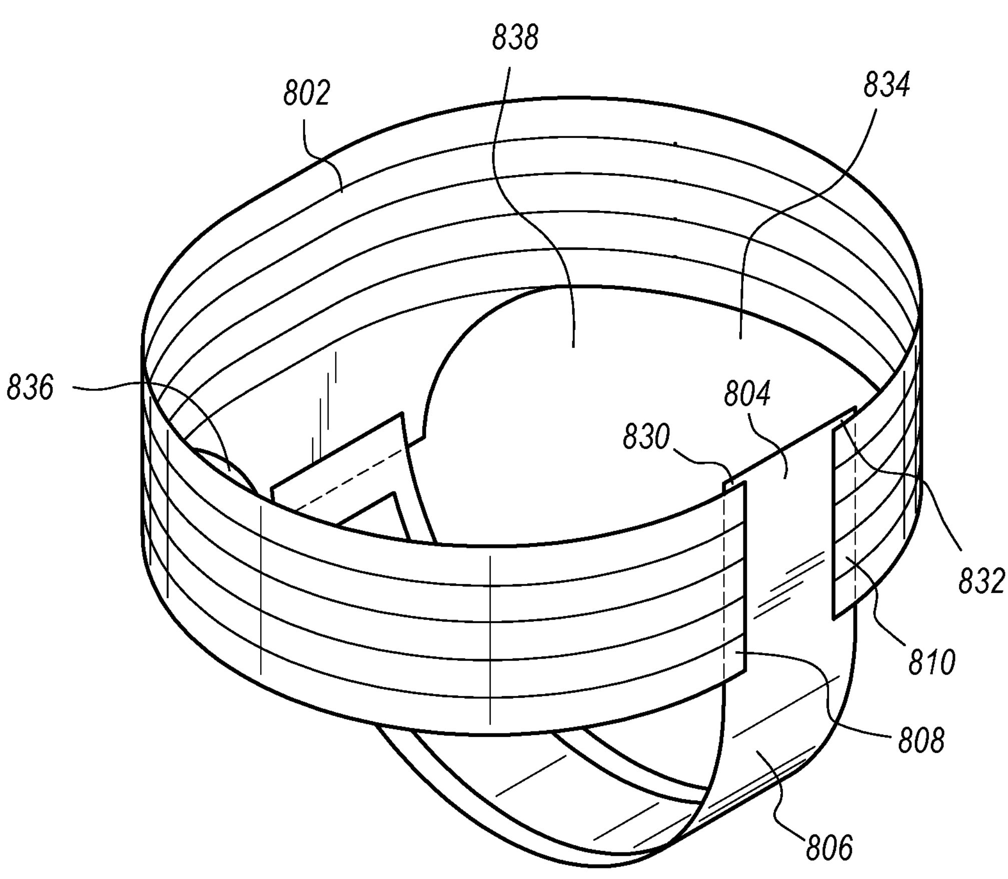
FIG. 20 is a perspective view of an embodiment of a protective underwear in a connected condition.

Accordingly, a wearer may put the protective underwear 800 on like regular underwear (pulling it up), as shown in FIG. 20, or like a diaper (placing the product between the legs and fastening). When the protective underwear 800 is applied like regular underwear, the protective underwear 800 creates a waist opening 834 with a first and a second leg opening 836, 838. Other features further provide leg openings that are more generous as a result of the rectangular chassis, rectangular body configuration allows for a more accurate fit to accommodate a wide range of body types per protective underwear size. With typical protective underwear, lacking refastenable sides, putting on a new pair requires a user to not have pants on and be naked on their bottom half. This means that the user must be in a seated or standing position to apply the protective underwear found in the prior art, which may prove difficult for the elderly or sickly. Additionally, a typical protective underwear presents difficulties when the underwear has been soiled and needs to be changed in public. In contrast, the refastenable protective underwear allows a user to apply the protective underwear with their pants around their ankles, rather than removing their pants and shoes. Further, it will be appreciated that the protective underwear 800, described herein, can be easily removed from a user and sealed shut once soiled. Without the ability to detach the sides of the protective underwear, a user would have to be naked on their bottom half and remove the soiled underwear by sliding them to the ankles and stepping out of the leg holes. This can create unnecessary mess and embarrassment for the user.

Figure 21:
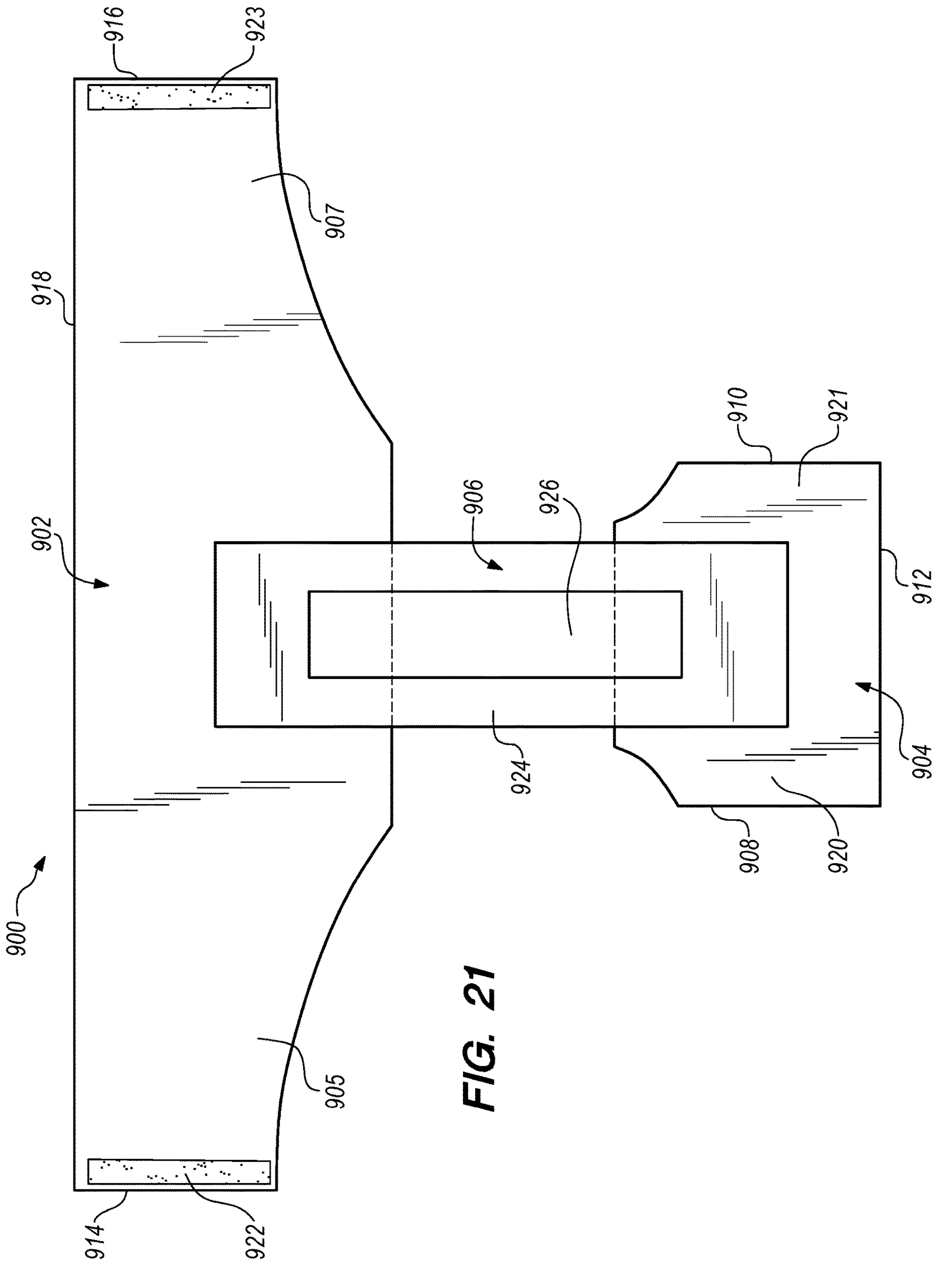
FIG. 21 is a plan view of an embodiment of a protective underwear in an open, flat condition with a first and a second chassis panel.

In one embodiment, as shown in FIG. 21, the protective underwear 900 in a substantially flat un-contracted state, having a reduced component configuration that accommodates multiple sized protective underwear users. The protective underwear 900 comprises a rear portion 902, a front portion 904, and a crotch portion 906 therebetween, and a plurality of laterally extending securement portions corresponding with a wearer's hip region. The front portion 904 defines a pair of laterally opposed side edges 908, 910 and a longitudinally opposed waist edge 912. The rear portion 902, generally positioned against the back of a user to cover the buttocks, defines a pair of laterally opposed side edges 914, 916 and longitudinally opposed waist edge 918. The rear portion 902 may comprise a first rear securement portion 922 operatively coupled to a first side portion 905, the first rear securement portion 922 having a width extending in a lateral direction from the first side portion 905 of the rear portion 902. Further, the rear portion 902 comprises a second rear securement portion 923, the second rear securement portion 923 having a width extending in a lateral direction from a second side portion 907. The front portion 904 may comprise a first and second front securement portion 920, 921. The first and second front securement portions 920, 921 may be on an outside surface, or an inside surface, of the front portion 904.

Further, the protective underwear 900 generally consists of several layers, including an inner layer 924, an absorbent layer 926, and a liquid impervious outer layer 928. The inner layer 924 faces a wearer and contacts the skin of the wearer when the protective underwear 900 is secured to the wearer. The inner layer 924 may be composed of a moisture-pervious fabric suitable to allow bodily discharge to pass through the inner layer and be absorbed by the absorbent layer. It will be understood that the inner layer 924 and the outer layer 928 of the first and second front securement portions 920, 921 may also receive the first and second rear securement portions 922, 923. For example, in some embodiments, the first and second securement portions 922, 923 may be attached to the outer layer 928 or outside surface of the front portion 904. In a further embodiment, the first and second rear securement portions 922, 923 may be attached to the inner layer 924. The front and rear securement portions 920, 921, 922, 923 may include any mechanical fastener, such as an adhesive, hook and loop, or any other means of securing the rear portion 902 to the front portion 904. When the protective underwear 900 is placed on a user, the outside surface of the front portion 904 is facing away from the user. This allows the outside surface of the front portion 904 to receive the first and second rear securement portions 922, 923 as they wrap around a user's hips and to the front of the user. It will be appreciated that a user may adjust and readjust the front and rear securement portions 920, 921, 922, 923 to get a custom fit.

The protective underwear 900 further includes the crotch portion 906. The crotch portion 906 has a substantially rectangular outer perimeter including a length extending in a longitudinal direction from the back to the front of a user and a width extending in a lateral direction. The crotch portion 906 may comprise portions of the inner layer 924, the absorbent layer 926, and the liquid impervious outer layer 928.

While the present invention has been described with reference to one or more particular embodiments, those skilled in the art will recognize that many changes may be made thereto without departing from the spirit and scope of the present invention. Furthermore, components from one embodiment can be used in other non-exclusive embodiments. By way of example, any of the features of FIG. 3 described herein can include any of the features described in FIGS. 8-11, 18-21. Similarly, each of the features of FIGS. 6-6A, 8-11, 18-19, and 21 depict one side of an absorbent article. It is to be understood that an unillustrated second side of an absorbent article may be a mirror image of the embodiments of FIGS. 6-6A, 8-11, 18-19, and 21 and thus will include each of the elements described herein. Each of these embodiments and obvious various thereof is contemplated as falling within the spirit and scope of the invention, which is set forth in the following alternative embodiments.

What is claimed is:

1. An absorbent article comprising:
- a chassis comprising an outer layer, an absorbent layer, and an inner layer, the chassis further comprising:
  - a first chassis portion comprising an attachment portion,
  - a second chassis portion comprising a first receiving portion, and a second receiving portion, and
  - a crotch portion extending between the first chassis portion and the second chassis portion; and
- a rear portion connected with chassis at the attachment portion, the rear portion comprising a first side portion attached to a first side of the second chassis portion to form a first leg opening and a second side portion attached to a second side of the second chassis portion to form a second leg opening;
- wherein the first side portion comprises a single, integral panel of material, is connected with the second chassis portion in an initial condition, is adapted to separate from the second chassis portion by tearing the first side portion panel of material, and is adapted to reconnect with the second chassis portion by overlapping the first side portion with the first receiving portion; and
- wherein the second side portion is adapted to separate from the second chassis portion and is adapted to reconnect with the second chassis portion by overlapping the second side portion with the second receiving portion.

2. The absorbent article of claim 1, wherein the first and second side portions are extensible.

3. The absorbent article of claim 1, wherein the rear portion is extensible.

4. The absorbent article of claim 1, wherein the chassis has a substantially rectangular outer perimeter.

5. The absorbent article of claim 1, wherein the chassis is an hourglass shape.

6. The absorbent article of claim 1, wherein the first receiving portion and the second receiving portion each comprise a sizing indicator; and wherein each sizing indicator comprises a perforation.

7. The absorbent article of claim 1, wherein the first receiving portion and the second receiving portion each comprise a sizing indicator; and wherein each sizing indicator comprises a visual indicia.

8. The absorbent article of claim 1, wherein the first receiving portion and the second receiving portion each comprise a sizing indicator; and wherein the first receiving portion sizing indicator is complementary to the second receiving portion sizing indicator.

9. The absorbent article of claim 1, wherein the first receiving portion and the second receiving portion each comprise a sizing indicator; and wherein the first receiving portion sizing indicator is substantially symmetrical to the second receiving portion sizing indicator.

10. The absorbent article of claim 1, wherein the first receiving portion and the second receiving portion each comprise a sizing indicator.

11. The absorbent article of claim 1, wherein the first side portion comprises a sizing indicator.

12. The absorbent article of claim 11, wherein the first side portion is torn at the sizing indicator.

13. An absorbent article comprising:
- a chassis comprising:
  - an outer layer,
  - an absorbent layer,
  - an inner layer,
  - a front portion comprising a receiving portion,
  - a rear portion, and
  - a crotch portion extending between the front portion and the rear portion;
- a side panel comprising a single sheet of material without a seam and attached to a side of the rear portion to form a leg opening;
- wherein the side panel is connected with the front portion in an initial condition, is adapted to separate from the front portion by tearing the sheet of material, and is adapted to reconnect with the front portion.

14. The absorbent article of claim 13, wherein the receiving portion comprises a cohesive material and the side panel reconnects with the front portion by engaging the cohesive material of the receiving portion.

15. An absorbent article comprising:
- a chassis comprising:
  - an outer layer,
  - an absorbent layer,
  - an inner layer,
  - a front portion comprising a receiving portion comprising a cohesive material,
  - a rear portion, and
  - a crotch portion extending between the front portions and the rear portion;
- a side panel comprising a sheet of material and attached to a side of the rear portion to form a leg opening;
- wherein the side panel is connected with the front portion in an initial condition, is adapted to separate from the front portion by tearing the sheet of material, and is adapted to reconnect with the front portion; and
- wherein the sheet of material comprises a sheet of cohesive material.

16. The absorbent article of claim 15, wherein the cohesive material of the side panel sheet of material is adapted to engage the cohesive material of the receiving portion.

17. An absorbent article comprising:

a chassis comprising:

an outer layer, an absorbent layer, an inner layer, a front portion comprising a receiving portion comprising a cohesive material, a rear portion, and a crotch portion extending between the front portion and the rear portion;

a side panel comprising a sheet of cohesive material and attached to a side of the rear portion to form a leg opening;

wherein the side panel is connected with the front portion in an initial condition, is adapted to separate from the front portion by tearing the sheet of cohesive material, and is adapted to reconnect with the front portion by engaging the cohesive material of the receiving portion without a secondary fastener.

18. The absorbent article of claim 17, wherein the sheet of cohesive material comprises a single, integral panel of material.

19. The absorbent article of claim 17, wherein the sheet of cohesive material comprises a single sheet of material without a seam.

20. The absorbent article of claim 17, wherein the sheet of cohesive material comprises a perforation, and wherein the side panel is adapted to separate from the front portion by tearing the sheet of cohesive material at the perforation.

* * * * *